(12) United States Patent
Yamada et al.

(10) Patent No.: US 8,076,348 B2
(45) Date of Patent: Dec. 13, 2011

(54) ACYLGUANIDINE DERIVATIVE OR SALT THEREOF

(75) Inventors: Hiroyoshi Yamada, Tokyo (JP); Hirotsune Itahana, Tokyo (JP); Ayako Moritomo, Tokyo (JP); Takaho Matsuzawa, Tokyo (JP); Eisuke Nozawa, Tokyo (JP); Shinobu Akuzawa, Tokyo (JP); Koichiro Harada, Okayama (JP)

(73) Assignee: Astellas Pharma Inc., Tokyo (JP)

( * ) Notice: Subject to any disclaimer, the term of this patent is extended or adjusted under 35 U.S.C. 154(b) by 756 days.

(21) Appl. No.: 11/997,956

(22) PCT Filed: Aug. 7, 2006

(86) PCT No.: PCT/JP2006/315576
§ 371 (c)(1),
(2), (4) Date: Feb. 5, 2008

(87) PCT Pub. No.: WO2007/018168
PCT Pub. Date: Feb. 15, 2007

(65) Prior Publication Data
US 2010/0168096 A1     Jul. 1, 2010

(30) Foreign Application Priority Data
Aug. 8, 2005   (JP) ............................. P.2005-230095

(51) Int. Cl.
*A61K 31/435*   (2006.01)
(52) U.S. Cl. ............ 514/277; 514/232.8; 514/290; 514/538; 514/411; 514/339; 548/427; 546/276.7; 546/15; 546/111; 544/142; 560/102
(58) Field of Classification Search ............ 548/441, 548/443, 446
See application file for complete search history.

(56) References Cited

U.S. PATENT DOCUMENTS
5,288,758 A   2/1994   Vidaluc et al.
(Continued)

FOREIGN PATENT DOCUMENTS
CA   2 537 079 A1   9/2005
(Continued)

OTHER PUBLICATIONS

Patani et al "Bioisosterim: A rational approach in drug design", Chem., Rev., 1996, vol. 98, No. 8, pp. 3147-3176.*

(Continued)

*Primary Examiner* — Brandon Fetterolf
*Assistant Examiner* — Jean Cornet
(74) *Attorney, Agent, or Firm* — Finnegan, Henderson, Farabow, Garrett & Dunner, LLP

(57) ABSTRACT

[Problem] To provide a compound which can be used in the prevention and/or treatment of diseases in which $5\text{-HT}_{2B}$ receptor and $5\text{-HT}_7$ receptor are concerned, particularly in the treatment of irritable bowel syndrome (IBS) and/or prevention of migraine.
[Means for Resolution] It was found that an acylguanidine derivative having a tricyclic structure or a pharmaceutically acceptable salt thereof has a strong antagonism to $5\text{-HT}_{2B}$ receptor and $5\text{-HT}_7$ receptor. In addition, the compound of the present invention having antagonism to both of the receptors showed superior pharmacological action in comparison with the case of the single use of an antagonist selective for either one of the receptors. Based on the above, the compound of the present invention is useful in preventing and/or treating diseases in which $5\text{-HT}_{2B}$ receptor and $5\text{-HT}_7$ receptor are concerned, particularly in treating irritable bowel syndrome (IBS) and/or preventing migraine.

13 Claims, 4 Drawing Sheets

U.S. PATENT DOCUMENTS

| | | | |
|---|---|---|---|
| 5,629,317 A | 5/1997 | Audia et al. | |
| 5,643,916 A | 7/1997 | Audia et al. | |
| 5,663,178 A | 9/1997 | Audia et al. | |
| 5,688,807 A | 11/1997 | Audia et al. | |
| 5,705,519 A | 1/1998 | Audia et al. | |
| 5,736,544 A | 4/1998 | Audia et al. | |
| 5,861,408 A | 1/1999 | Audia et al. | |
| 5,861,409 A | 1/1999 | Audia et al. | |
| 5,861,410 A | 1/1999 | Audia et al. | |
| 5,869,691 A | 2/1999 | Audia et al. | |
| 5,886,004 A | 3/1999 | Audia et al. | |
| 6,440,988 B1 | 8/2002 | Craig | |
| 6,444,477 B1 | 9/2002 | Borman et al. | |
| 6,482,822 B1 | 11/2002 | Bigg et al. | |
| 6,514,968 B1 * | 2/2003 | TenBrink | 514/232.8 |
| 6,534,535 B1 | 3/2003 | Zhu et al. | |
| 7,098,233 B2 | 8/2006 | Di Cesare et al. | |
| 7,402,680 B2 | 7/2008 | Carruthers et al. | |
| 2003/0027128 A1 | 2/2003 | Borman et al. | |
| 2004/0235899 A1 | 11/2004 | Maria Assunta et al. | |
| 2004/0266775 A1 | 12/2004 | Kleemann et al. | |
| 2005/0119295 A1 | 6/2005 | Carruthers et al. | |
| 2005/0148632 A1 | 7/2005 | Tokumasu et al. | |
| 2008/0161419 A1 | 7/2008 | Akuzawa | |
| 2008/0171788 A1 | 7/2008 | Akuwaza et al. | |
| 2008/0200551 A1 | 8/2008 | Yamada | |
| 2009/0036421 A1 | 2/2009 | Seo et al. | |
| 2009/0062363 A1 | 3/2009 | Kaku et al. | |

FOREIGN PATENT DOCUMENTS

| | | |
|---|---|---|
| EP | 0 309 422 A2 | 3/1989 |
| EP | 0 622 356 | 11/1994 |
| EP | 0 639 573 A1 | 2/1995 |
| EP | 1 264 820 A1 | 12/2002 |
| EP | 1 541 172 | 6/2005 |
| EP | 1 716 867 A1 | 11/2006 |
| EP | 1 852 129 A1 | 11/2007 |
| JP | 5-194359 | 8/1993 |
| JP | 9-510216 | 10/1997 |
| JP | 11-506468 | 6/1999 |
| JP | 2004-534816 | 11/2004 |
| JP | 2005-162657 | 6/2005 |
| JP | 2008-048671 | 3/2008 |
| WO | WO 96/39382 | 12/1996 |
| WO | WO 98/55115 | 6/1998 |
| WO | WO 99/20599 | 4/1999 |
| WO | WO 00/17191 | 3/2000 |
| WO | WO 01/68585 A1 | 9/2001 |
| WO | WO 02/056010 A2 | 7/2002 |
| WO | WO 2004/014428 A1 | 2/2004 |
| WO | WO 03/000252 A1 | 11/2004 |
| WO | WO 2005/040169 A2 | 5/2005 |
| WO | WO 2005/079845 A1 | 9/2005 |
| WO | WO 2005/080322 A1 | 9/2005 |
| WO | WO 2006/085510 A1 | 8/2006 |

OTHER PUBLICATIONS

D. Hoyer et al., "International Union of Pharmacology Classification of Receptors for 5-Hydroxytryptamine (Serotonin)," *Pharmacological Reviews*, vol. 46, No. 2, pp. 157-203 (1994).

C. P. Bearcroft et al., "Postprandial Plasma 5-Hydroxytryptamine in Diarrhoea Predominant Irritable Bowel Syndrome: A Pilot Study," *Gut*, vol. 42, pp. 42-46 (1998).

D.-Y. Kim, "Serotonin: A Mediator of the Brain-Gut Connection," *The American Journal of Gastroenterology*, vol. 95, No. 10, pp. 2698-2709 (2000).

N. J. Talley, "Pharmacologic Therapy for the Irritable Bowel Syndrome," *The American Journal of Gastroenterology*, vol. 98, No. 4, pp. 750-758 (2003).

F. De Ponti et al., "Irritable Bowel Syndrome (New Agents Targeting Serotonin Receptor Subtypes)," *Drugs*, vol. 61, No. 3, pp. 317-332 (2001).

R. A. Borman et al., "Functional Evidence for a 5-HT$_{2B}$ Receptor Mediating Contraction of Longitudinal Muscle in Human Small Intestine," *British Journal of Pharmacology*, vol. 114, pp. 1525-1527 (1995).

R. A. Borman et al., "5-HT$_{2B}$ Receptors Play a Key Role in Mediating the Excitatory Effects of 5-HT in Human Colon in vitro," *British Journal of Pharmacology*, vol. 135, pp. 1144-1151 (2002).

D. Carter et al., "Characterization of a Postjunctional 5-HT Receptor Mediating Relaxation of Guinea-pig Isolated Ileum," *European Journal of Pharmacology*, vol. 280, pp. 243-250 (1995).

H. Liu et al., "Expression Patterns of 5-HT$_7$ Receptor Isoforms in the Rat Digestive Tract," *Life Sciences*, vol. 69, pp. 2467-2475 (2001).

B. Tuladhar et al., "5-HT$_7$ Receptors Mediate the Inhibitory Effect of 5-HT on Peristalsis in the Isolated Guinea-pig Ileum," *British Journal of Pharmacology*, vol. 138, pp. 1210-1214 (2003).

E. J. Mylecharane, "5-HT$_2$ Receptor Antagonists and Migraine Therapy," *Journal of Neurology*, vol. 238, pp. S45-S52 (1991).

K. W. Johnson et al., "Neurogenic Dural Protein Extravasation Induced by Meta-Chlorophenylpiperazine (mCPP) Involves Nitric Oxide and 5-HT$_{2B}$ Receptor Activation," *Cephalalgia*, vol. 23, pp. 117-123 (2003).

P. Manivet et al., "PDZ-dependent Activation of Nitric-oxide Synthases by the Serotonin 2B Receptor," *The Journal of Biological Chemistry*, vol. 275, No. 13, pp. 9324-9331 (2000).

E. P. Wei et al., "Calcitonin Gene-Related Peptide Mediates Nitroglycerin and Sodium Nitroprusside-Induced Vasodilation in Feline Cerebral Arterioles," *Circulation Research*, vol. 70, No. 6, pp. 1313-1319 (1992).

D. W. Bonhaus et al., "RS-127445, A Selective 5-HT$_{2B}$ Receptor Antagonist, Blocks mCPP-Evoked Plasma Protein Extravasation in dura mater and Capsaicin-Evoked *c-fos* Expression in Trigeminal Nucleus Caudalis of Rat," *Cluster Headache & Related Conditions*, J. Olesen et al., eds., Oxford University Press, pp. 278-286 (1999).

J. Terrón et al., 5-HT$_7$ Receptor mRNA Expression in Human Trigeminal Ganglia, *Neuroscience Letters*, Vo. 302, pp. 9-12 (2001).

J. Terrón, "Is the 5-HT$_7$ Receptor Involved in the Pathogenesis and Prophylactic Treatment of Migraine?" *European Journal of Pharmacology*, vol. 439, pp. 1-11 (2002).

P. Pierce et al., "Dual Effect of the Serotonin Agonist, Sumatriptan, on Peripheral Neurogenic Inflammation," *Regional Anesthesia*, vol. 21, No. 3, pp. 219-225 (1996).

European Search Report dated Sep. 9, 2009.

Office Action dated Nov. 6, 2009 from a corresponding Mexican application.

Office Action dated Jun. 7, 2010, from corresponding European application No. 06782418.5.

Non-final Office Action mailed Nov. 8, 2010, for U.S. Appl. No. 10/589,892.

Extended European Search Report dated Jun. 17, 2009, for related European Application No. 06 713 158.1, related to co-pending U.S. Appl. No. 11/883,651.

English language Abstract of JP 9-510216.

Bonhaus, Douglas W.; Flippin, Lee A.; Greenhouse, Robert J.; Jaime, Saul; Rocha, Cindy; Dawson, Mark; Van Natta, Kristine; Chang, L.K.; Pulido-Rios, Tess; Webber, Andrea; Leung, Edward; Eglen, Richard M.; and Martin, Graeme R., "RS-127445: a selective, high affinity, orally bioavailable 5-HT$_{2B}$ receptor antagonist", British Journal of Pharmacology, 1999, 127, pp. 1075-1082.

D. W. Bonhaus, et al., "RS-127445, a selective 5-HT$_{2B}$ receptor antagonist, blocks mCPP-evoked plasma protein extravasation in dura mater and capsaicin-evoked c-fos expression in trigeminal nucleus caudalis of rat," vol. 9, (United Kingdom), Oxford University Press, 1999, pp. 278-286.

Lovell, Peter J.; Bromidge, Steven M.; Dabbs, Steven; Duckworth, D. Malcolm; Forbes, Ian T.; Jennings, Andrew J.; King, Frank D.; Middlemiss, Derek N.; Rahman, Shirley K.; Saunders, Damian V.; Collin, Lissa L.; Hagan, Jim J.; Riley, Graham J. and Thomas, David R., "A Novel, Potent, and Selective 5-HT$_7$ Antagonist: (*R*)-3-(2-(2-(4-Methylpiperidin-1-yl)-ethyl)pyrrolidine-1-sulfonyl)phenol(SB-269970)", J. Med. Chem. 2000, 43, pp. 342-345.

Naughton, Marie; Mulrooney, Jane B., and Leonard, Brian E., "A Review of the Role of Serotonin Receptors in Psychiatric Disorders", Human Psychopharmacology, Clinical and Experimental., Vol. 15, No. 6, 2000, pp. 397-415.

Parsons, Andrew A., and Strijbos, Paul J.L.M., "The neuronal versus vascular hypothesis of migraine and cortical spreading depression", Current Opinion in Pharmacology, Elsevier Science Publisher, vol. 3, No. 1, pp. 73-77.

K. Schmuck, et al., "Activation of Meningeal 5-HT$_{2B}$ Receptors: An Early Step in the Generation of Migraine Headache?", European Journal of Neuroscience, vol. 8 (1996), pp. 959-967.

J. A. Terrón, "Involvement of the 5-HT$_7$ Receptor in Craniovascular Vasodilatation: Potential Impact in Migraine," Proc. West. Pharmacol. Soc., vol. 41 (1998), pp. 247-251.

Terrón, José A., & Falcón-Neri, Alicia, "Pharmacological evidence for the 5-HT$_7$ receptor mediating smooth muscle relaxation in canine cerebral arteries", British Journal of Pharmacology, 127, 1999, pp. 609-616.

Whorwell, P.J. et al., "Bladder Smooth Muscle Dysfunction in Patients with Irritable Bowel Syndrome", Gut, vol. 27 (1986), pp. 1014-1017.

Copending U.S. Appl. No. 10/568,684, filed Feb. 17, 2006, Abandoned Aug. 18, 2009.

International Search Report for PCT/JP2006/302015, mailed Apr. 18, 2006.

Translation of Written Opinion of International Search Authority for International Application No. PCT/JP 2005/002950, which is related to copending U.S. Appl. No. 10/568,684.

Translation of International Preliminary Report on Patentability for International Application No. PCT/JP 2005/002950, which is related to copending U.S. Appl. No. 10/568,684.

Co-Pending U.S. Appl. No. 11/883,651, filed Aug. 3, 2007.

Office Action for related U.S. Appl. No. 11/883,651, dated Sep. 29, 2010.

Office Action for related U.S. Appl. No. 10/589,892, dated Jun. 28, 2010.

Response to Office Action for related U.S. Appl. No. 10/589,892, dated Jun. 28, 2010, dated Sep. 28, 2010.

Office Action for related U.S. Appl. No. 11/883,651, dated Dec. 9, 2009.

Response to Office Action for related U.S. Appl. No. 11/883,651, dated Dec. 9, 2009, dated Mar. 9, 2010.

Supplementary European Search Report dated Aug. 20, 2009, for European Application No. 05710598.3, which is related to Co-Pending U.S. Appl. No. 10/589,892.

Office Action for related Chinese Patent Application No. 200680029586.8, dated Jul. 30, 2010.

European Office Action dated Sep. 13, 2010 in EP 06713158.1-1223/1852129.

Final Office Action dated Apr. 7, 2011 in U.S. Appl. No. 11/883,651.

Office Action dated Nov. 11, 2010, in U.S. Appl. No. 10/589,891.

Office Action dated Dec. 6, 2010, in U.S. Appl. No. 12/279,221.

Office Action dated Dec. 10, 2010 in Russian App. No. 2008137612/04(048427) which corresponds to U.S. Appl. No. 12/279,221.

Office Action dated Apr. 11, 2011 in U.S. Appl. No. 12/278,609.

Kitano, Masafumi, Synthesis and Biological Activity of N-(Aminoiminomethyl)-1H-Indole Carboxamide Derivatives as NA$^+$/H$^+$ Exchanger Inhibitors, Chem. Pharm. Bull. 47(11) 1999, 1538-1548.

Kuroita, T. et al., Design and Synthesis of 6-Chloro-3,4-dihydro-4-methyl-2H-1,4-benzoxazine-8-carboxamide Derivatives as Potent Serotonin-3 (5-HT$_3$ Receptor Antagonists, 1996, Chem. Pharm. Bull., 44(4), 756-764.

Lopez-Rodriguez, Maria L. et al., Benzimidazole Derivatives. 3. 3D-QSAR/coMFA Model and Computational Simulation for the Recognition of 5-HT$_4$ Receptor Antagonists, 2002, J. Med. Chem., 45, 4806-4815.

Mylecharane, E.J., 5-HT$_2$ Receptor Antagonists and Migraine Therapy, J Neurol, 1991, 238: S45-S52.

Response to Office Action dated Dec. 6, 2010 in U.S. Appl. No. 12/279,221.

Summons to Attend Oral Proceedings dated Sep. 13, 2010, for European Application No. 06 713 158.1.

Theoharides et al., Expert Opinion Pharmacotherapy, (2008), 9(17), pp. 2979-2994.

Tuladhar, Bishwa R.; Ge, Lanbo & Naylor, Robert J., "5-HT$_7$ receptors mediate the inhibitory effect of 5-HT on peristalsis in the isolated guinea-pig ileum", British Journal of Pharmacology, vol. 138, 2003, pp. 1210-1214.

* cited by examiner

[Fig. 1]
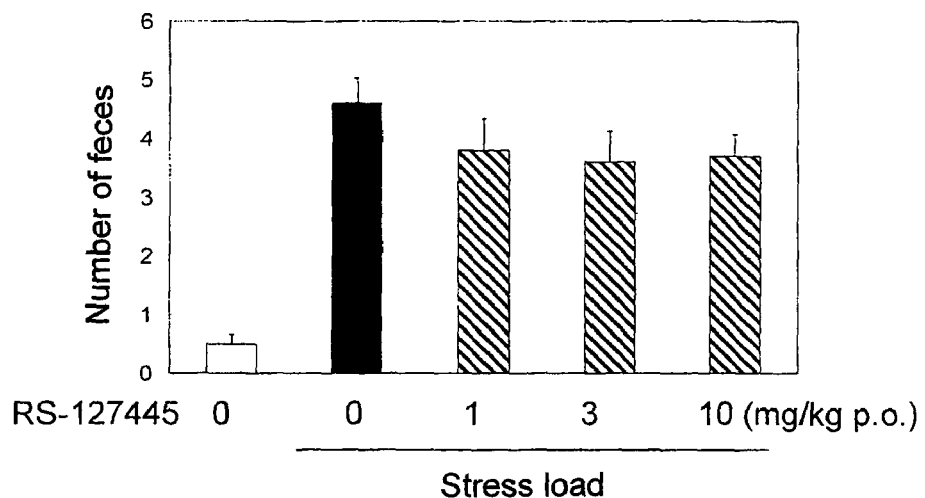
[Fig. 2]
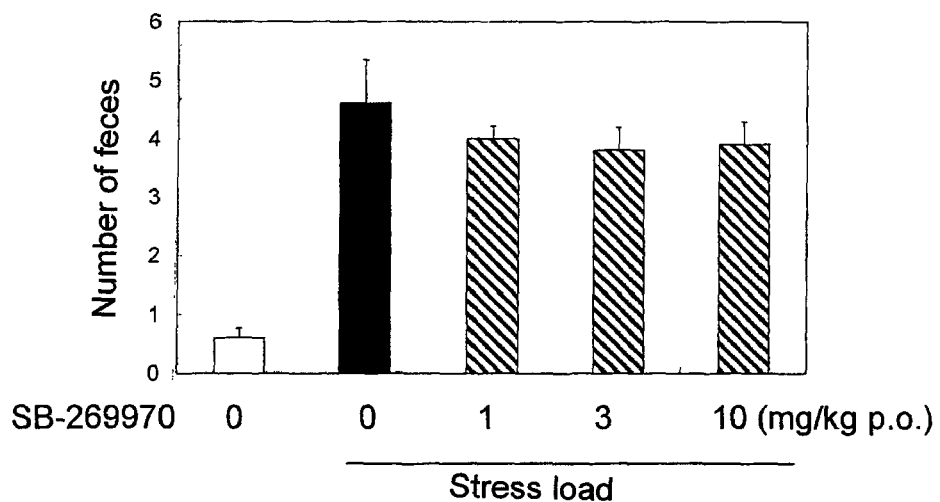

[Fig. 3]
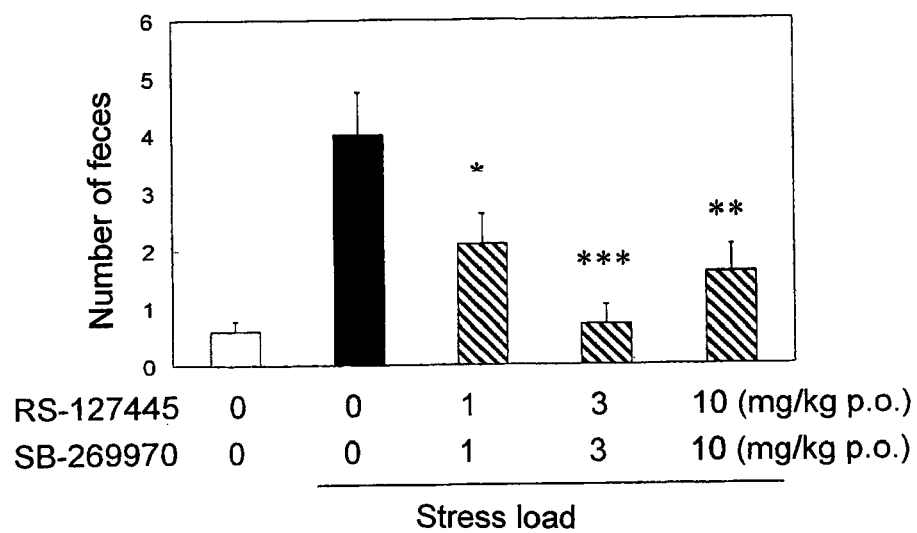
[Fig. 4]
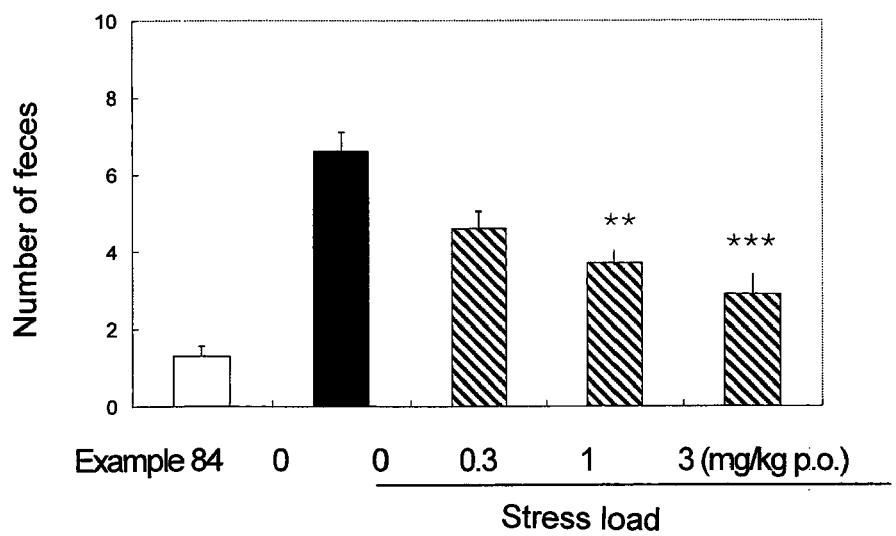

[Fig. 5]
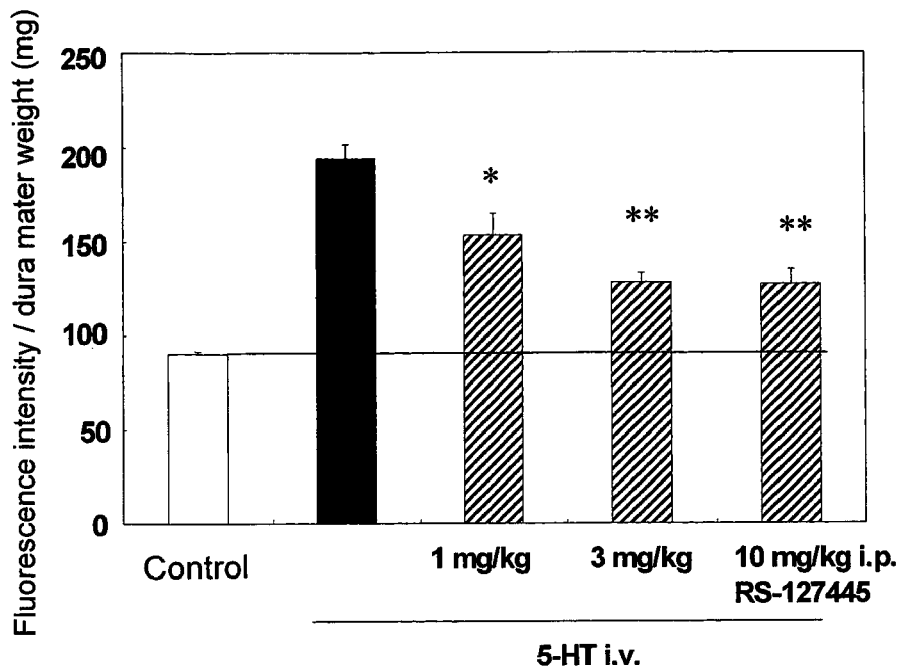
[Fig. 6]
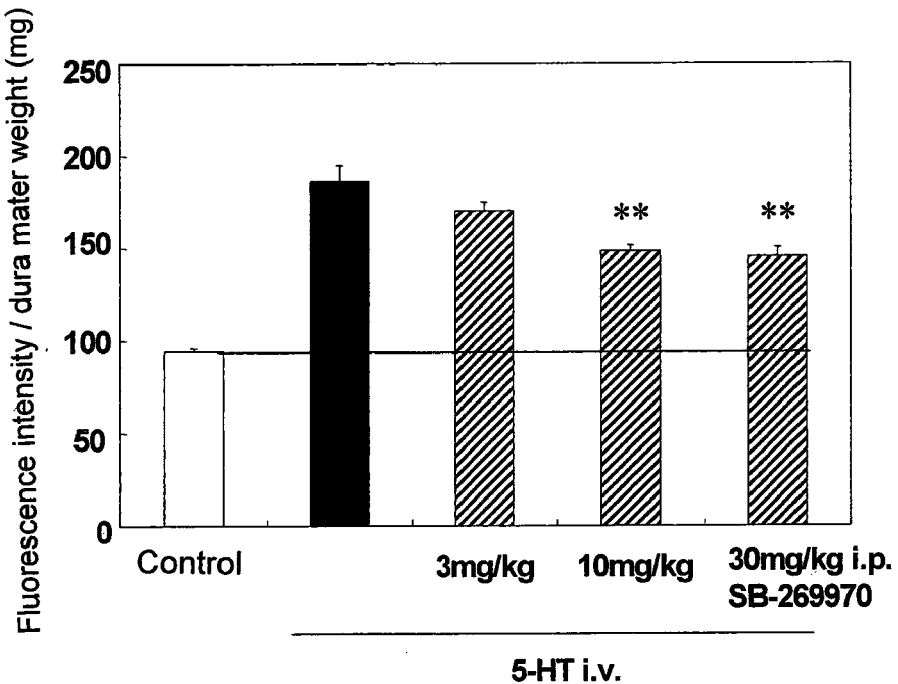

[Fig. 7]
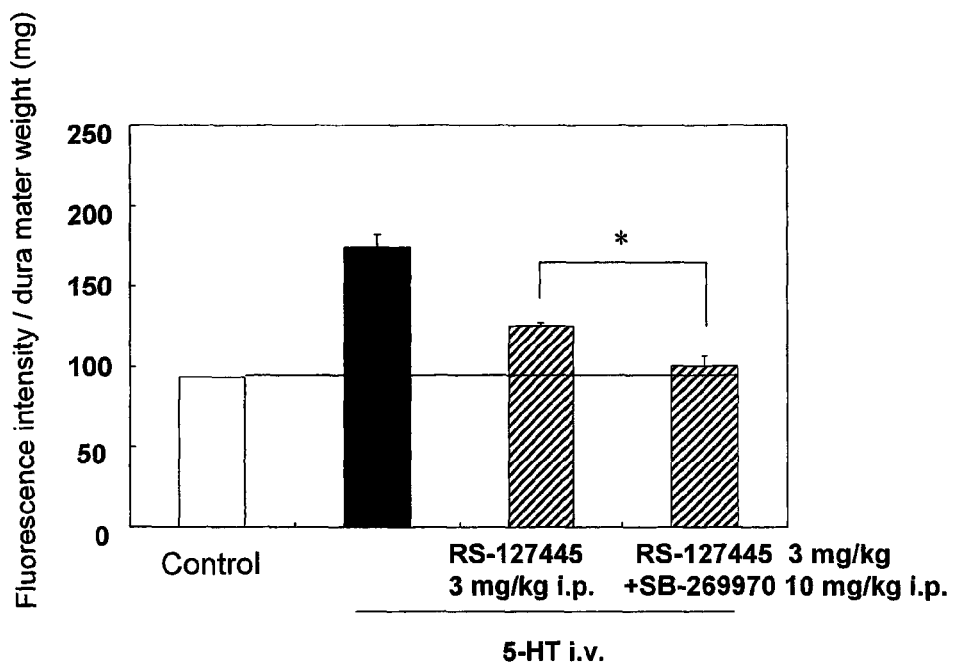
[Fig. 8]
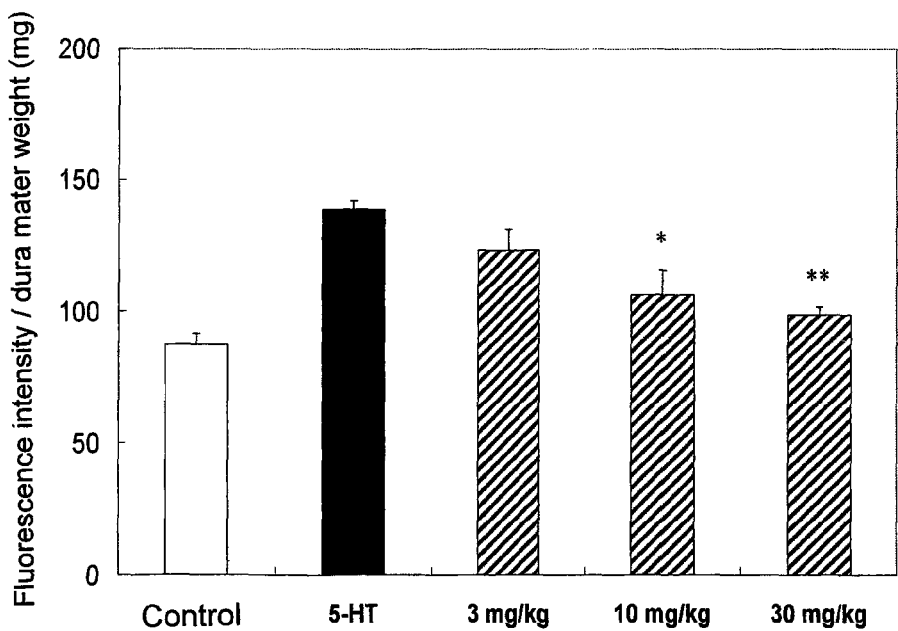

ACYLGUANIDINE DERIVATIVE OR SALT THEREOF

TECHNICAL FIELD

The present invention relates to a pharmaceutical, particularly an acylguanidine derivative which is useful as an agent for treating irritable bowel syndrome and/or an agent for preventing migraine.

BACKGROUND OF THE INVENTION

Serotonin (5-HT) is a monoamine neurotransmitter and exerts various physiological actions via 5-HT receptors. The 5-HT receptors are classified into 7 families of from $5\text{-}HT_1$ to $5\text{-}HT_7$. Particularly, three subtypes, $5\text{-}HT_{2A}$, $5\text{-}HT_{2B}$, and $5\text{-}HT_{2C}$, are known for $5\text{-}HT_2$ receptor (Non-patent Reference 1).

Irritable bowel syndrome (IBS) is a disease in which abdominal pain or abdominal unpleasantness continues for a long period of time. Based on the symptoms, IBS is classified into a diarrhea-predominant-type, a constipation-predominant-type and a diarrhea-constipation alternating-type. In each case, it has been pointed out that there is a causal relation between morbid state and amount of 5-HT in blood. For example, there is a report pointing out that increase of blood 5-HT concentration after meal occurs in patients of diarrhea-predominant IBS and this deeply relates to the morbid state (Non-patent Reference 2).

Currently, a 5-HT receptor antagonist or a 5-HT receptor agonist is already used in Europe and U.S.A. as an agent for treating IBS, though it is at a clinical trial stage in Japan. Alosetron ($5\text{-}HT_3$ receptor antagonist) is used in the clinical field as an agent for treating diarrhea-predominant-type, but side effects such as ischemic colitis, constipation and the like have been reported. In addition, tegaserod ($5\text{-}HT_4$ receptor agonist) is used in the clinical field in Europe and U.S.A. as an agent for treating constipation-predominant-type, but its side effects have also been reported (Non-patent References 3 and 4).

In recent years, pharmacological studies on other 5-HT receptor subtypes have also been in progress (Non-patent Reference 5). Regarding the $5\text{-}HT_{2B}$ receptor and $5\text{-}HT_7$ receptor, there are reports pointing out about said receptors and roles in the digestive tracts. For example, there are reports stating that the $5\text{-}HT_{2B}$ receptor is localized in human ileum longitudinal muscle and a $5\text{-}HT_{2B}$ receptor antagonistic compound suppresses contraction by 5-HT (Non-patent Reference 6) and that the $5\text{-}HT_{2B}$ receptor localizing in human colon relates to the 5-HT-induced contraction at the time of electric stimulation and a $5\text{-}HT_{2B}$ receptor antagonistic compound suppresses it (Non-patent Reference 7).

In addition, there are reports stating that the $5\text{-}HT_7$ receptor is present in guinea pig small intestines (Non-patent Reference 8) and rat intestines (Non-patent Reference 9) and concerned in the peristalsis of guinea pig ileum (Non-patent Reference 10). Based on the above, it is expected that a compound having antagonism to $5\text{-}HT_{2B}$ and $5\text{-}HT_7$ receptors is useful as an agent for treating IBS.

On the other hand, migraine is a pulsating headache which is a disease in which a strong pain occurs in one side or both sides of the head and continues for several hours to about 3 days. It is suggested that morbid state of migraine progresses by the following onset mechanism. That is, dura mater blood vessel once contracts by the action of neurotransmitters (e.g., 5-HT and the like) and then dilates again and, at this time, releases vasoactive peptides (e.g., calcitonin gene-related peptide (CGRP) and the like) and serum protein to accelerate inflammation which leads to the onset of headache.

The pharmaceutical targeted at migraine is divided into a preventive agent and a treating agent. The former aims at reducing attack frequency by preventively administering it continuously before onset of the disease and the latter aims at suppressing the pain by taking it after expression of the attack. As the preventive agent for migraine, Ca antagonists (e.g., lomerizine, flunarizine and the like), 5-HT antagonists (e.g., pizotifen, methysergide and the like), β-adrenergic blocking agents (e.g., propranolol and the like), and the like are clinically used in certain countries, but many side effects have been reported on them and sufficient clinical effects have not been obtained.

Regarding the pizotifen as a 5-HT antagonist among the preventive agents described in the above, its efficacy is high in comparison with other agents, but there is a problem in that fatigued feeling, drowsiness, dizziness, weight gain and the side effects are observed at its effective dose (Non-patent Reference 11). It is known that said compound has affinity for all of the 5-HT receptor subtypes and also has high affinity for various receptors such as $\alpha_1$ adrenaline receptor ($\alpha_1$), muscarine 1 receptor ($M_1$), dopamine 2 receptor ($D_2$) and the like.

In recent years, pharmacological studies on 5-HT receptor subtypes have been conducted. It has been reported that a $5\text{-}HT_{2B}$ receptor antagonist suppresses guinea pig m-chlorophenylpiperazine (mCPP)-induced dura mater extravascular protein leakage (Non-patent Reference 12) and that the $5\text{-}HT_{2B}$ receptor localizing on the vascular smooth muscle induces release of nitrogen monoxide (NO) and the NO accelerates release of neuro-peptides such as CGRP, substance P and the like from the trigeminal nerve (Non-patent References 13 and 14). Also, a result which suggests a migraine preventive action has been obtained by an animal model using a $5\text{-}HT_{2B}$ receptor selective antagonist (Non-patent Reference 15). Also, there are reports stating that $5\text{-}HT_7$ receptor is present in the trigeminal nerve (Non-patent Reference 16), concerned in the vasodilation by 5-HT in cerebrovascular smooth muscle (Non-patent Reference 17) or concerned in the dura mater extravascular protein leakage acceleration action (Non-patent Reference 18). In addition, it has been reported in Patent References 1 and 2, applied by the instant applicant and published after the priority date of this application, that a selective $5\text{-}HT_{2B}$ and $5\text{-}HT_7$ receptor dual antagonist is effective for preventing migraine. Based on the above, it is expected that a compound which has the antagonistic activity for $5\text{-}HT_{2B}$ and $5\text{-}HT_7$ receptors and is selective against other receptors is useful as an agent for preventing migraine with less side effects.

As the compound having antagonistic activity for $5\text{-}HT_{2B}$ and $5\text{-}HT_7$ receptors, the compounds shown in Patent References 1 and 2 have been reported.

It has been reported in Patent References 1 and 2, applied by the instant applicant and published after the priority date of this application, that a fluorene compound represented by the following formula (A) has antagonistic activity for $5\text{-}HT_{2B}$ and $5\text{-}HT_7$ receptors and is effective for preventing migraine.

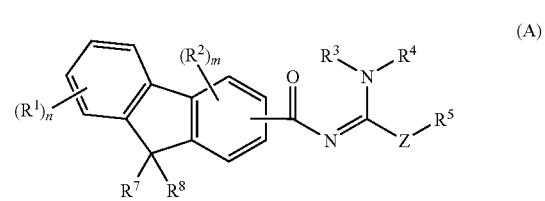

As acylguanidine derivatives having a tricyclic structure, Patent References 3 and 4 are known.

Patent Reference 3 describes that the compounds represented by the following formula (B) is effective for the treatment of central diseases. However, in these compounds, a ring group is linked to the guanidine moiety via a linker X.

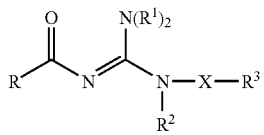
(B)

(In the formula, R is a cycloalkyl, an aryl, a mono- to tricyclic heteroaryl or the like, $R^1$ and $R^2$ are independently H, an alkyl, alkenyl or the like, X is a bond, an alkene, an alkenylene or the like, and $R^3$ is a cycloalkyl, an aryl, an alkylaryl or the like. See said publication for details.)

In Patent Reference 4, it is reported that the compounds represented by the following formula (C) have an NO synthase inhibitory activity and/or an active oxygen species scavenging activity. However, there is no illustrative disclosure in this publication on a compound in which Φ is a bond or a compound which has —NH$_2$ as —NR$^{13}$R$^{14}$.

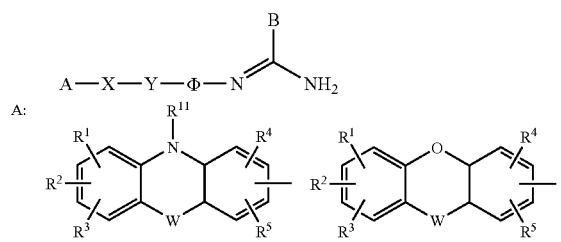

(In the formula, Φ is a bond or phenylene group, B is —CH$_2$—NO$_2$, an alkyl group, an aryl group or NR$^{13}$R$^{14}$ or the like, wherein R$^{13}$ and R$^{14}$ are independently hydrogen atom, an alkyl group, cyano group or the like, X is a bond, —O—, —S— or CO— or the like, Y is a bond, —(CH$_2$)$_m$ or the like, W is not present, or a bond, S atom or NR$^{15}$, and R$^1$ to R$^5$ are hydrogen, a halogen or the like. See said publication for details.)

Non-patent Reference 1: Pharmacological Reviews, (USA), 1994, vol. 46, p. 157-203
Non-patent Reference 2: Gut, (England), 1998, vol. 42, p. 42-46
Non-patent Reference 3: The American Journal of Gastroenterology, (USA), 2000, vol. 95, p. 2698-2709
Non-patent Reference 4: The American Journal of Gastroenterology, (USA), 2003, vol. 98, p. 750-758
Non-patent Reference 5: Drugs, (New Zealand), 2001, vol. 61, no. 3, p. 317-332
Non-patent Reference 6: Brutish Journal of Pharmacology, (England), 1995, vol. 114, p. 1525-1527
Non-patent Reference 7: Brutish Journal of Pharmacology, (England), 2002, vol. 135, p. 1144-1151
Non-patent Reference 8: European Journal of Pharmacology, (Holland), 1995, vol. 280, p. 243-250
Non-patent Reference 9: Life Science, (Holland), 2001, vol. 69, p. 2467-2475
Non-patent Reference 10: Brutish Journal of Pharmacology, (England), 2003, vol. 138, p. 1210-1214
Non-patent Reference 11: Journal of Neurology, (Germany), 1991, vol. 238, p. S45-S52
Non-patent Reference 12: Cephalalgia, (England), 2003, vol. 23, p. 117-123
Non-patent Reference 13: The Journal of Biological Chemistry, (USA), 2000, vol. 275, p. 9324-9331
Non-patent Reference 14: Circulation Research, (USA), 1992, vol. 70, p. 1313-1319
Non-patent Reference 15: "Cluster Headache and Related Conditions", edited by D. W. Bonhaus, vol. 9, (England), Oxford University Press, 1999, p. 278-286
Non-patent Reference 16: Neuroscience Letters, (Holland), 2001, vol. 302, p. 9-12
Non-patent Reference 17: European Journal of Pharmacology, (Holland), 2002, vol. 439, p. 1-11
Non-patent Reference 18: Regional Anesthesia, (England), 1996, vol. 21, p. 219-225
Patent Reference 1: International Publication No. 2005/79845
Patent Reference 2: International Publication No. 2005/80322
Patent Reference 3: International Publication No. 99/20599
Patent Reference 4: International Publication No. 00/17191

DISCLOSURE OF THE INVENTION

Problems that the Invention is to Solve

As has been described in the above, the existing agents for treating IBS and agents for preventing migraine are not satisfactory in view of the efficacy, safety and the like, so that it is highly demanded to provide an agent for treating IBS and an agent for preventing migraine, having excellent efficacy and safety.

Means for Solving the Problems

As has been described in the above, it is be expected that a compound having antagonistic activity to 5-HT$_{2B}$ and 5-HT$_7$ receptors becomes an IBS treating agent and/or a migraine preventing agent having less side effects and excellent efficacy. Accordingly, with the aim of providing a compound useful as an IBS treating agent and/or a migraine preventing agent, the present inventors have conducted intensive studies on a compound having antagonistic activity to 5-HT$_{2B}$ and 5-HT$_7$ receptors. As a result, it was found that novel acylguanidine derivatives represented by the following general formula (I), which are characterized by the possession of a tricyclic structure, show excellent antagonism to both of the 5-HT$_{2B}$ and 5-HT$_7$ receptors. The present invention has been accomplished by further finding that these acylguanidine derivatives have excellent IBS treating effect and/or migraine preventing effect in comparison with the conventional compounds which have the antagonistic activity to only one of the 5-HT$_{2B}$ and 5-HT$_7$ receptors.

That is, the present invention relates to an acylguanidine derivative represented by the following general formula (I) or a pharmaceutically acceptable salt thereof

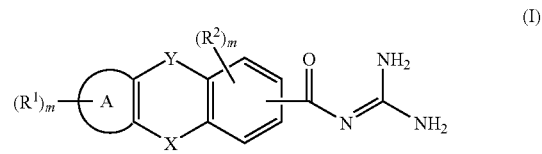
(I)

[symbols in the formula represent the following meanings
$R^1$ and $R^2$: the same or different from each other, and each represents lower alkyl which may be substituted, lower alkenyl, halogen, —CN, —NO$_2$, —OR$^0$, —O-halogeno-lower alkyl, —OC(O)R⁰, —NR⁰R⁰ᵃ, —NR⁰—C(O)R⁰ᵃ, —NR⁰—S(O)₂R⁰ᵃ, —SH, —S(O)$_p$-lower alkyl, —S(O)₂—NR⁰R⁰ᵃ, —C(O)R⁰, —CO₂R⁰, —C(O)NR⁰R⁰ᵃ, cycloalkyl, aryl or a hetero ring group,
wherein the aryl and a hetero ring group in R¹ and R² may respectively be substituted,
R⁰ and R⁰ᵃ: the same or different from each other, and each represents —H or lower alkyl,
m, n and p: the same or different from one another and each is 0, 1 or 2,
X: —C(R³)(R⁴)— or —N(R⁵)—,
Y: (i) when X is —C(R³)(R⁴)—: a single bond,
(ii) when X is —N(R⁵)—: a single bond or —O—,
R³ and R⁴: the same or different from each other, and each represents —H, lower alkyl which may be substituted, halogen, —OR⁰, —NR⁰R⁰ᵃ, —NR⁰—C(O)R⁰ᵃ, —SH or —S(O)$_p$-lower alkyl,
or R³ and R⁴ may together form oxo, lower alkylene-O—, —O-lower alkylene-O—, lower alkylene-S—, —S-lower alkylene-S—, or lower alkylene which may be interrupted by 1 or 2 groups selected from —O—, —NR⁰— and —S(O)$_p$—,
R⁵: —H, lower alkyl which may be substituted, —C(O)R⁰, —CO₂R⁰, —C(O)NR⁰R⁰ᵃ, —S(O)$_p$-lower alkyl, —S(O)$_p$-aryl, cycloalkyl, a hetero ring group, lower alkylene-cycloalkyl, lower alkylene-aryl, lower alkylene-hetero ring group,
—C(O)-aryl or —C(O)-hetero ring group,
wherein the aryl and hetero ring group in R⁵ may be respectively substituted,
ring A: (i) when X is —C(R³)(R⁴)—: cycloalkene ring or 5- to 8-membered monocyclic hetero ring,
(ii) when X is —N(R⁵)—: benzene ring, cycloalkene ring or 5- to 8-membered monocyclic hetero ring;
the same shall apply hereinafter].

In addition, the present invention also relates to a pharmaceutical composition which comprises the aforementioned acylguanidine derivative or a pharmaceutically acceptable salt thereof and a pharmaceutically acceptable carrier, particularly a pharmaceutical composition which is a 5-HT$_{2B}$ and 5-HT$_7$ receptor antagonist, a migraine preventing agent and/or an IBS treating agent.

That is, (1) a pharmaceutical composition which comprises the compound described in the formula (I) or a pharmaceutically acceptable salt thereof and a pharmaceutically acceptable carrier.
(2) The pharmaceutical composition described in (1), which is a 5-HT$_{2B}$ and 5-HT$_7$ receptor antagonist.
(3) The pharmaceutical composition described in (1), which is a migraine preventing agent.
(4) The pharmaceutical composition described in (1), which is an IBS treating agent.
(5) Use of the compound described in the formula (I) or a pharmaceutically acceptable salt thereof for the manufacture of a 5-HT$_{2B}$ and 5-HT$_7$ receptor antagonist, a migraine preventing agent and/or an IBS treating agent.
(7) A method for preventing migraine and/or treating IBS, which comprises administering a therapeutically effective amount of the compound described in the formula (I) or a salt thereof to a patient.

Advantage of the Invention

The compound of the present invention showed excellent antagonistic activity to both of the 5-HT$_{2B}$ and 5-HT$_7$ receptors. In addition, since the compound of the present invention showed excellent IBS treating effect and/or migraine preventing effect in comparison with the conventional compounds which have the antagonistic activity to only one of the 5-HT$_{2B}$ and 5-HT$_7$ receptors, it is useful as an IBS treating agent and/or migraine preventing agent.

BRIEF DESCRIPTION OF THE DRAWINGS

FIG. 1 is a graph showing a result of the measurement of the number of feces at the time of PS-127445 administration in the rat confined stress defecation model of the test method (4). Significant difference was not found in the respective 1, 3 and 10 mg/kg administration groups in comparison with the non-administration group (N=10).
FIG. 2 is a graph showing a result of the measurement of the number of feces at the time of SB-269970 administration in the rat confined stress defecation model of the test method (4). Significant difference was not found in the respective 1, 3 and 10 mg/kg administration groups in comparison with the non-administration group (N=10).
FIG. 3 is a graph showing a result of the measurement of the number of feces at the time of RS-127445 and SB-269970 simultaneous administration in the rat confined stress defecation model of the test method (4). Statistical test was carried out by the Dunnett's method, and * shows a significance level of 5%, and  that of 1% and * that of 0.1% (N=10).
FIG. 4 is a graph showing a result of the measurement of the number of feces at the time of the administration of Example 84 in the rat confined stress defecation model of the test method (4). Statistical test was carried out by the Dunnett's method, and  shows 1% and * shows 0.1% (N=10).
FIG. 5 is a graph showing a result of the measurement of the leaked amount of protein at the time of RS-127445 administration in the guinea pig migraine model of the test method (5). Statistical test was carried out by the Dunnett's method, and * shows a significance level of 5%, and ** that of 1%.
FIG. 6 is a graph showing a result of the measurement of the leaked amount of protein at the time of SB-269970 administration in the guinea pig migraine model of the test method (5). Statistical test was carried out by the Dunnett's method, and ** shows a significance level of 1%.
FIG. 7 is a graph showing a result of the measurement of the leaked amount of protein at the time of RS-127445 and SB-269970 simultaneous administration in the guinea pig migraine model of the test method (5). Statistical test was carried out by the T test, and * shows a significance level of 5%.
FIG. 8 is a graph showing a result of the measurement of the leaked amount of protein at the time of the administration of the compound of Example 1 in the guinea pig migraine model of the test method (5). Statistical test was carried out by the T test, and * shows a significance level of 5%.

BEST MODE FOR CARRYING OUT THE INVENTION

The following describes the present invention in detail.
In this description, the term "lower" means a straight or branched hydrocarbon chain having from 1 to 6 carbon atoms unless otherwise noted.
The "lower alkyl" means a $C_{1-6}$ alkyl. Illustratively, methyl, ethyl, normal-propyl, isopropyl, normal-butyl, isobutyl, sec-butyl, tert-butyl, normal-pentyl, normal-hexyl and the like may be exemplified. Preferred is a $C_{1-4}$ alkyl, and particularly preferred are methyl, ethyl, normal-propyl and isopropyl.
The "lower alkenyl" means a $C_{2-6}$ alkenyl. The double bond may be at any optional position, and it may have two or more double bonds. Illustratively, for example, vinyl, 1-propenyl, allyl, isopropenyl, 1-butenyl, 2-butenyl, 3-butenyl, 1,3-butadienyl, 1-pentenyl, 1-hexenyl and the like may be cited. Preferred is a $C_{2-4}$ alkenyl, and particularly preferred are vinyl, 1-propenyl, allyl and isopropenyl.

The "lower alkylene" means a divalent group resulting from the removal of one hydrogen at an optional position of $C_{1-6}$ alkyl. Illustratively, methylene, ethylene, methylmethylene, dimethylmethylene, trimethylene, propylene, butylene, pentylene, hexylene and the like may be exemplified. Preferred is a $C_{1-4}$ alkylene, and particularly preferred are methylene and ethylene.

The "halogen" means a halogen atom. Illustratively, fluoro, chloro, bromo and iodo may be cited. Preferred are fluoro and chloro.

The "halogeno-lower alkyl" means a group in which 1 or more optional hydrogen atoms of the aforementioned "lower alkyl" are substituted by the aforementioned "halogen" which are the same or different from one another. Illustratively, fluoromethyl, difluoromethyl, trifluoromethyl, 2,2,2-trifluoroethyl, pentafluoroethyl, hexafluoropropyl and the like may be exemplified. Preferred is a $C_{1-2}$ alkyl substituted by 1 to 5 fluoro, and particularly preferred is trifluoromethyl.

The "cycloalkyl" means a $C_{3-10}$ non-aromatic hydrocarbon ring group which may form a bridged ring or spiro ring or may be partially unsaturated. Illustratively, cyclopropyl, cyclobutyl, cyclopentyl, cyclohexyl, cycloheptyl, cyclooctyl, adamantyl, norbornyl, cyclopentenyl, cyclohexenyl and the like may be exemplified. Preferred is a $C_{3-7}$ cycloalkyl, and particularly preferred are cyclobutyl, cyclopentyl and cyclohexyl.

The "cycloalkene ring" in the ring A means a $C_{5-8}$ monocyclic non-aromatic hydrocarbon ring having a double bond at the fused site with the ring containing X and Y, which may further have a double bond. Illustratively, cyclopentene, cyclohexene, cycloheptene, cyclooctene and the like may be exemplified. Preferred are cyclopentene and cyclohexene.

The "aryl" means a monocyclic to tricyclic $C_{6-14}$ aromatic hydrocarbon ring group. Illustratively, for example, phenyl, naphthyl, anthranyl and the like may be cited. Preferred are phenyl and naphthyl. In addition, a $C_{5-8}$ non-aromatic hydrocarbon ring may be ring-fused and may form, for example, indanyl or tetrahydronaphthyl.

The "hetero ring group" means a saturated, unsaturated or partially unsaturated 3- to 8-membered monocyclic hetero ring group, 8- to 14-membered bicyclic hetero ring group or 11- to 20-membered tricyclic hetero ring group, which contains 1 to 4 hetero atoms selected from O, S and N. It may form oxide or dioxide through the oxidation of the S or N as the ring atom, or may form a bridged ring or spiro ring. As the monocyclic hetero ring group, illustratively, azetidinyl, oxiranyl, oxetanyl, pyrrolidinyl, piperidinyl, piperazinyl, morpholinyl, pyranyl, pyridyl, pyridazinyl, pyrimidinyl, pyrazinyl, furyl, dihydrofuryl, thienyl, pyrrolyl, oxazolyl, isoxazolyl, oxadiazolyl, thiazolyl, thiadiazolyl, imidazolyl, triazolyl, tetrazolyl, tetrahydrofuranyl, tetrahydropyranyl and the like may be exemplified. As the bicyclic hetero ring group, illustratively, indolyl, benzofuranyl, dihydrobenzofuranyl, benzothienyl, benzoxazolyl, benzimidazolyl, benzothiazolyl, quinolinyl, quinazolinyl, quinoxalinyl, cinnolinyl and the like may be exemplified. As the tricyclic hetero ring group, illustratively, carbazolyl, acridinyl and the like may be exemplified. Preferred are azetidinyl, oxiranyl, oxetanyl, pyrrolidinyl, piperidinyl, piperazinyl, morpholinyl, pyranyl, pyridyl, pyridazinyl, pyrimidinyl, pyrazinyl, furyl and thienyl, and particularly preferred are pyrrolidinyl, piperidinyl, piperazinyl, morpholinyl, pyranyl, pyridyl, pyridazinyl, pyrimidinyl, pyrazinyl, furyl and thienyl.

The "5- to 8-membered monocyclic hetero ring" in the ring A means an unsaturated or partially unsaturated 5- to 8-membered monocyclic hetero ring which contains 1 to 4 hetero atoms selected from O, S and N and has a double bond at the fused site with the ring containing X and Y. Illustratively, pyridine, pyridazine, pyrimidine, imidazole, furan, thiophene, oxazole, thiazole, tetrahydropyridine and the like. Preferred is a 5- or 6-membered monocyclic hetero ring, and particularly preferred are thiophene, pyridine and tetrahydropyridine.

The "lower alkylene which may be interrupted by 1 or 2 groups selected from —O—, —NR$^O$— and —S(O)$_p$—" formed by R$^3$ and R$^4$ in combination means a group formed by inserting 1 or 2 groups selected from —O—, —NR$^O$— and —S(O)$_p$— into the carbon-carbon bond of lower alkylene. When 2 groups are inserted, the respective groups may be the same or different from each other. Illustratively,
—CH$_2$—O—CH$_2$CH$_2$—, —CH$_2$—S—CH$_2$CH$_2$—, —CH$_2$—NH—CH$_2$CH$_2$—, —CH$_2$—N(CH$_3$)—CH$_2$CH$_2$—, —CH$_2$CH$_2$—O—CH$_2$CH$_2$—, —CH$_2$CH$_2$—S—CH$_2$CH$_2$—, —CH$_2$CH$_2$—NH—CH$_2$CH$_2$—, —CH$_2$CH$_2$—N(CH$_3$)—CH$_2$CH$_2$—, —CH$_2$—O—(CH$_2$)$_3$—, —CH$_2$—S—(CH$_2$)$_3$—, —CH$_2$—NH—(CH$_2$)$_3$—, —CH$_2$—N(CH$_3$)—(CH$_2$)$_3$—, —CH$_2$—O—CH$_2$—O—CH$_2$— and the like may be exemplified.

The "which may be substituted" means that it is "not substituted" or "substituted with 1 to 5 substituents which may be the same or different from one another".

According to the description, the acceptable substituent of the term "which may be substituted" may be any one as long as it is generally used in said technical field as a substituent of respective group. In addition, when two or more groups are present like the case, for example, of the lower alkyl of —C(O)—N(lower alkyl)$_2$, the respective substituents may be the same or different from each other.

Preferred as the substituents of the "lower alkyl which may be substituted" in R$^1$, R$^2$, R$^3$, R$^4$ and R$^5$ are halogen, —OR$^O$, —O-lower alkylene-aryl, —OC(O)R$^O$, —NR$^O$R$^{Oa}$, —NR$^O$—C(O)R$^{Oa}$, —NR$^O$—S(O)$_2$R$^{Oa}$, —SH, —S(O)$_p$-lower alkyl, —S(O)$_2$—NR$^O$R$^{Oa}$, —C(O)R$^O$, —CO$_2$R$^O$ or —C(O)NR$^O$R$^{Oa}$. Particularly preferred is halogen, —OR$^O$ or —NR$^O$R$^{Oa}$.

Preferred as the substituent of the "aryl" and "hetero ring group" which may be respectively substituted in R$^1$, R$^2$ and R$^5$ is halogen, lower alkyl which may be substituted with halogen or aryl, —OR$^O$ or —O-halogeno-lower alkyl. Particularly preferred is halogen or lower alkyl.

Preferred embodiments of the present invention are shown below.

Preferred as R$^1$ is halogen, lower alkyl, —O-lower alkyl, —NH$_2$, lower alkylene-OR$^O$ or —C(O)H, and more preferred is halogen, lower alkyl, —O-lower alkyl, lower alkylene-OH or —C(O)H.

Preferred as R$^2$ is halogen or lower alkyl.

Preferred as m is 0 or 1, more preferably 0.

Preferred as n is 0.

Preferred as R$^3$ and R$^4$ are the case wherein they are the same or different from each other and each is lower alkyl or —OR$^O$, or the case wherein they mean oxo, lower alkylene-O— or —S-lower alkylene-S— in combination. More preferred as R$^3$ and R$^4$ is lower alkyl or —OR$^O$, or lower alkylene-O— or —S-lower alkylene-S— as R$^3$ and R$^4$ in combination, and further preferred is lower alkylene-O— as R$^3$ and R$^4$ in combination.

Preferred as R$^5$, when Y is a single bond, is —H, lower alkyl, lower alkylene-OR$^O$, cycloalkyl, lower alkylene-cycloalkyl, a hetero ring group, lower alkylene-(hetero ring group which may be substituted with lower alkyl), —C(O)- lower alkyl, —S(O)$_2$-lower alkyl or —C(O)—N(lower alkyl)$_2$, more preferred is lower alkyl, cycloalkyl, lower alkylene-cycloalkyl, a hetero ring group, lower alkylene-(hetero ring group which may be substituted with lower alkyl), —C(O)-lower alkyl or —S(O)$_2$-lower alkyl, and further more preferred is lower alkyl. When Y is —O—, preferred as R$^5$ is —H; lower alkyl, cycloalkyl, a hetero ring group or lower alkylene-(hetero ring group which may be substituted with lower alkyl), more preferred is lower alkyl, cycloalkyl, a hetero ring group or lower alkylene-(hetero ring group which may be substituted with lower alkyl), and further more preferred is lower alkyl.

Preferred as ring A, when X is —C(R$^3$)(R$^4$)—, is thiophene or pyridine, and more preferred is thiophene. When X is —N(R$^5$)—, preferred as ring A is benzene, thiophene or pyridine, and more preferred is benzene.

Preferred as X is —C(R$^3$)(R$^4$)— or —N(R$^5$)—.

Preferred as Y is a single bond.

Preferred as the tricyclic system constituted from ring A, a ring containing X and Y and benzene ring is carbazole, phenoxazine, indeno[2,1-b]thiophene or indeno[2,1-c]pyridine, more preferred is indeno[2,1-b]thiophene or indeno[2,1-c]pyridine, and further more preferred is indeno[2,1-b]thiophene.

In the aforementioned tricyclic system, preferred as the substitution position of the guanidinocarbonyl group is the para position against Y. Illustratively, it is the 2-position in the case of carbazole and phenoxazine, the 6-position in indeno[2,1-b]thiophene and the 7-position in indeno[2,1-c]pyridine.

A compound further consisting of the combination of the preferred groups described in the above is more desirable.

In addition, other preferred embodiments of the compound of the present invention represented by the general formula (I) are shown below.

(1) The compound described in the general formula (I), wherein X is —C(R$^3$)(R$^4$)—.

(2) The compound described in (1), wherein ring A is thiophene or pyridine.

(3) The compound described in (2), wherein the tricyclic system constituted from ring A, a ring containing X and Y and benzene ring is indeno[2,1-b]thiophene or indeno[2,1-c]pyridine.

(4) The compound described in (3), wherein the substitution position of the guanidinocarbonyl group is the para position against Y.

(5) The compound described in (4), wherein R$^3$ and R$^4$ are the same or different from each other and each is lower alkyl or —OR$^0$, or oxo, lower alkylene-O— or —S-lower alkylene-S— as R$^3$ and R$^4$ in combination.

(6) The compound described in the general formula (I), wherein X is —N(R$^5$)—.

(7) The compound described in (6), wherein Y is a single bond.

(8) The compound described in (7), wherein ring A is benzene.

(9) The compound described in (8), wherein the substitution position of the guanidinocarbonyl group is the para position against Y.

(10) The compound described in (9), wherein R$^5$ is lower alkyl, cycloalkyl, lower alkylene-cycloalkyl, a hetero ring group, lower alkylene-(hetero ring group which may be substituted with lower alkyl), —C(O)-lower alkyl or —S(O)$_2$-lower alkyl.

(11) The compound described in (6), wherein Y is —O—.

(12) The compound described in (11), wherein ring A is benzene.

(13) The compound described in (12), wherein the substitution position of the guanidinocarbonyl group is the para position against Y.

(14) The compound described in (13), wherein R$^5$ is lower alkyl, cycloalkyl, a hetero ring group or lower alkylene-(hetero ring group which may be substituted with lower alkyl).

(15) A compound described in the general formula (I) selected from the group consisting of
N-(diaminomethylene)-4,5-dihydro-3H-spiro[furan-2,4'-indeno[1,2-b]thiophene]-6'-carboxamide,
N-(diaminomethylene)-9-isopropyl-9H-carbazole-2-carboxamide,
N-(diaminomethylene)-10-isopropyl-10H-phenoxazine-2-carboxamide,
N-(diaminomethylene)spiro[1,3-dithiolan-2,4'-indeno[1,2-b]thiophene]-6'-carboxamide, and
N-(diaminomethylene)-4-methoxy-4-methyl-4H-indeno[1,2-b]thiophene]-6-carboxamide, or a pharmaceutically acceptable salt thereof.

In addition, according to the description, the "binding affinity" means the ability to bind to a part of a receptor, and its evaluation is carried out by comparing the Ki value calculated by an in vitro receptor binding test as described in the test method or the IC$_{50}$ value of a receptor binding test carried out under the same condition as occasion demands. In this connection, when the IC$_{50}$ value cannot be calculated because sufficient inhibitory action is not shown at a certain concentration in the receptor binding test, IC$_{50}$ value of the compound is regarded as said concentration or more in some cases.

When binding affinity of the compound of the present invention is "selective" for the 5-HT$_{2B}$ and 5-HT$_7$ receptors, it means that binding affinity of said receptors is high in comparison with the binding affinity for "other receptors". The "selective" according to the present invention indicates a case in which the Ki value or IC$_{50}$ value showing binding affinity for said receptors is 1/10 or less in comparison with the value for the "other receptors", and this value is preferably 1/50 or less, more preferably 1/100 or less, more further preferably 1/500 or less, particularly preferably 1/1000 or less.

The "other receptors" as used herein are other receptors which are reported regarding the existing nonselective 5-HT receptor antagonists and receptors particularly relating to undesirable actions. Thus, preferred as the compound of the present invention is a compound whose binding affinity for 5-HT$_{2B}$ and 5-HT$_7$ receptors is selective in comparison with α$_1$, M$_1$ and D$_2$ receptors, and more preferred is a compound whose binding affinity for 5-HT$_{2B}$ and 5-HT$_7$ receptors is selective in comparison with α$_1$, M$_1$, D$_2$, 5-HT$_{1A}$, 5-HT$_{1B}$, 5-HT$_{2A}$, 5-HT$_{2C}$, 5-HT$_3$, 5-HT$_4$ and 5-HT$_6$ receptors.

There is a case in which geometrical isomers and tautomers are present in the compound (I) of the present invention. For example, the following tautomers are present.

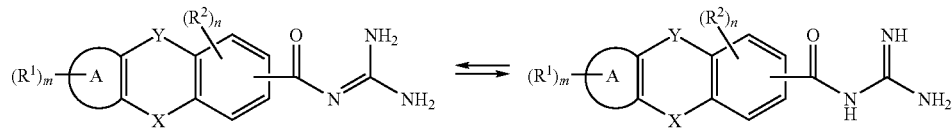

The present invention includes one of such tautomers or a mixture thereof.

In addition, there is a case in which isomers based on the asymmetric carbon atom are present in the compound of the present invention. The present invention includes mixtures and isolated counterparts of these optical isomers.

In this connection, all of the compounds which are converted into the compound (I) or a salt thereof by undergoing metabolism in the living body, or so-called prodrugs, are included in the compound (I) of the present invention. Regarding the group which forms this prodrug, the groups described in "Progress in Medicine", Lifescience Medica, 1985, vol. 5, p. 2157-2161 and the groups described in "Iyakuhin no Kaihatsu (Development of Medicines)", published in 1990 by Hirokawa Shoten, vol. 7 Bunshi Sekkei (Molecular Design) 163-198 may be exemplified.

As the pharmaceutically acceptable salt of the compound (I) of the present invention, illustratively, acid addition salts with inorganic acids (e.g., hydrochloric acid, hydrobromic acid, hydroiodic acid, sulfuric acid, nitric acid, phosphoric acid and the like), organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like), and the like may be exemplified. Also, there is a case in which it forms a salt with a base depending on the kind of substituent, and for example, salts with inorganic bases containing metals such as sodium, potassium, magnesium, calcium, aluminum and the like or organic bases (e.g., methylamine, ethylamine, ethanolamine, lysine, ornithine and the like), ammonium salt, and the like may be cited.

In addition, the present invention also includes various hydrates, solvates and polymorphic substances of the compound (I) and salts thereof.

(Production Methods)

The compound (I) of the present invention and pharmaceutically acceptable salts thereof can be produced by employing various conventionally known synthetic methods by making use of the characteristics based on its basic backbone or kinds of its substituents. In that case, depending on the kinds of functional group, there is a case in which protection of said functional group with an appropriate protecting group or its replacement to a group which can be easily converted into said functional group, at the stages of the starting materials to intermediates, is effective in view of the production techniques. As such a functional group, it includes amino group, hydroxyl group, carboxyl group and the like, as their protecting groups, the protecting groups described for example in "Protective Groups in Organic Synthesis", edited by T. W. Greene and 3rd edition, John Wiley & Sons, 1999 may be cited, and these may be optionally selected and used in response to the reaction conditions. By such a method, a desired compound can be obtained by carrying out the reaction by introducing said protecting group and then removing the protecting group or converting it into a desired group as occasion demands.

The following describes typical production methods of the compound of the present invention.

(Production method 1)

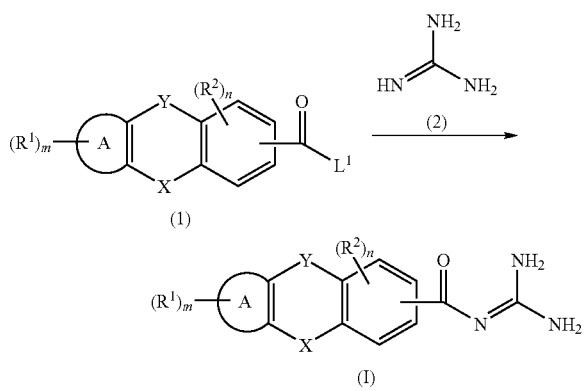

($L^1$ represents —OH or a leaving group.)

This production method is a method in which the compound (I) of the present invention is produced by subjecting a carboxylic acid or a reactive derivative thereof (1) and guanidine (2) or a salt thereof to amidation.

The reaction can be carried out using equivalent amounts of the carboxylic acid or a reactive derivative thereof (1) and guanidine (2), or guanidine in an excess amount. It can be carried out under cooling to under heating, preferably at from −20° C. to 60° C., in a solvent which is inert to the reaction, such as aromatic hydrocarbons (e.g., benzene, toluene or xylene or the like), halogenated hydrocarbons (e.g., dichloromethane, 1,2-dichloroethane or chloroform or the like), ethers (e.g., diethyl ether, tetrahydrofuran (THF), dioxane or dimethoxyethane (DME) or the like), N,N-dimethylformamide (DMF), dimethyl sulfoxide (DMSO), ethyl acetate, acetonitrile or water, or a mixed liquid thereof.

When a free carboxylic acid wherein $L^1$ is OH is used as the starting compound (1), it is desirable to carry out the reaction in the presence of a condensing agent. In that case, it is desirable to use a condensing agent such as N,N'-dicyclohexylcarbodiimide (DCC), 1-[3-(dimethylamino)propyl]-3-ethylcarbodiimide (WSC), 1,1'-carbonyldiimidazole (CDI), 2-(1H-benzothiazol-1-yl)-1,1,3,3-tetramethyluronium hexafluorophosphate (HBTU), diphenyl phosphoryl azide (DPPA), phosphorous oxychloride or the like, and further an additive agent (e.g., N-hydroxysuccinimide (HONSu), 1-hydroxybenzotriazole (HOBt) or the like). It can be carried out using equivalent amount or excess amount of the condensing agent based on the carboxylic acid.

As the reactive derivative of carboxylic acid wherein $L^1$ is a leaving group regarding the starting compound (1), an acid halide (e.g., acid chloride, acid bromide or the like), an acid anhydride (e.g., a mixed acid anhydride with phenyl chlorocarbonate, p-toluenesulfonic acid, isovaleric acid or the like or symmetric acid anhydride), an active ester (e.g., an ester which can be prepared using phenol that may be substituted with an electron withdrawing group such as a nitro group, a fluorine atom or the like, HOBt, HONSu and the like), a lower alkyl ester and the like may be exemplified, and each of them can be produced from respective carboxylic acid using a reaction obvious to those skilled in the art. Depending on the kind of the reactive derivatives, it is sometimes advantageous for smooth progress of the reaction to carry out the reaction in the presence of a base (e.g., organic bases such as triethylamine, diisopropylethylamine, N-methylmorpholine, pyridine, 4-(N,N-dimethylamino)pyridine and the like or inorganic bases such as sodium bicarbonate). Pyridine can also serve as a solvent. In this connection, when a lower alkyl ester is used as the reactive derivative, it is desirable to carry out the reaction under room temperature to under heating under reflux.

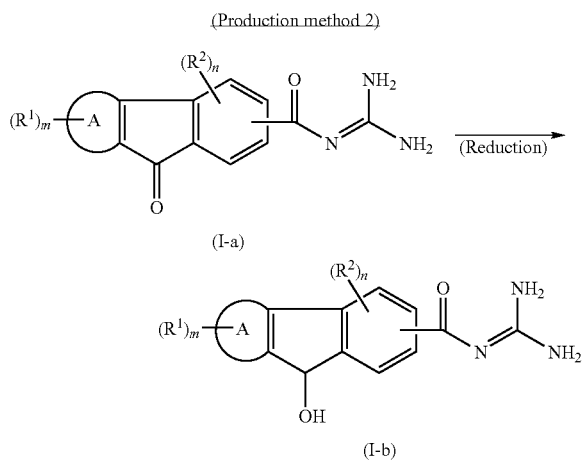

Among the compound (I) of the present invention, a compound (I-b) in which —$CR^3R^4$— is represented by —CH(OH)— can be produced by subjecting a compound (I-a) of the present invention in which said moiety is a carbonyl group to reduction.

The reaction is carried out by treating the compound (I-a) with an equivalent amount or excess amount of a reducing agent. As the reducing agent, hydride reducing agents such as sodium borohydride or diisobutylaluminum hydride or the like or the reducing agent described in "Comprehensive Organic Transformation", edited by Richard C. Larock, (USA), VCH Publishers, Inc., 1989, are used. The reaction is carried out under cooling to under heating, preferably at from −20° C. to room temperature with using as a solvent selected from aromatic hydrocarbons, ethers, DMF, DMSO, alcohols (e.g., methanol, ethanol, and the like), or water, or mixed solvents thereof.

(Production Method 3, Other Production Methods)

The compounds of the present invention having various functional groups such as an amino group, a carboxyl group, an amido group, a hydroxyl group, an alkylamino group and the like can be easily produced by those methods which are obvious to those skilled in the art or modified methods thereof using the compounds of the present invention having a corresponding nitro group, ester group, carboxyl group, amino group and the like as the starting materials. For example, these can be produced by the following reactions.

3-a: Reduction (1)

A compound having an amino group can be produced by reducing a compound having a nitro group. For example, the reaction can be carried out using a hydrogenation reaction which uses palladium-carbon, Raney nickel or the like as the catalyst.

3-b: Reduction (2)

A compound having a hydroxyalkyl group can be produced by reducing a compound having an ester group. For example, the reaction may be carried out using lithium aluminum hydride, sodium borohydride or the like as the reducing agent.

3-c: Hydrolysis

A compound having a carboxyl group can be produced by hydrolyzing a compound having an ester group. For example, this may be carried out in accordance with the deprotection reaction described in the aforementioned "Protective Groups in Organic Synthesis".

3-d: Amidation

A compound having an amido group may be produced by the amidation of a compound having a carboxyl group or an amino group. This may be carried out in accordance with the aforementioned production method 1.

3-e: Alkylation

A compound having an alkylamino group can be produced by alkylating a compound having an amino group. As the alkylation reaction, the reaction can be carried out by a general method using various alkylating agents (e.g., an alkyl halide, an alkyl sulfonic acid ester or the like). In addition, a compound having an alkylamino group can be produced by carrying out reductive alkylation of a compound having an amino group with a carbonyl compound. The method described in "Jikken Kagaku Koza (Experimental Chemistry Course) (vol. 20) Yuki Gosei (Organic Synthesis) 2", edited by The Chemical Society of Japan, 4$^{th}$ edition, Maruzen, 1992, p. 300, or the like can be applied to the reaction.

(Production of Starting Compounds)

The starting compound (I) in the production methods described in the above can be produced for example by the following method, a conventionally known method or a modified method thereof.

(Starting Material Synthesis 1)

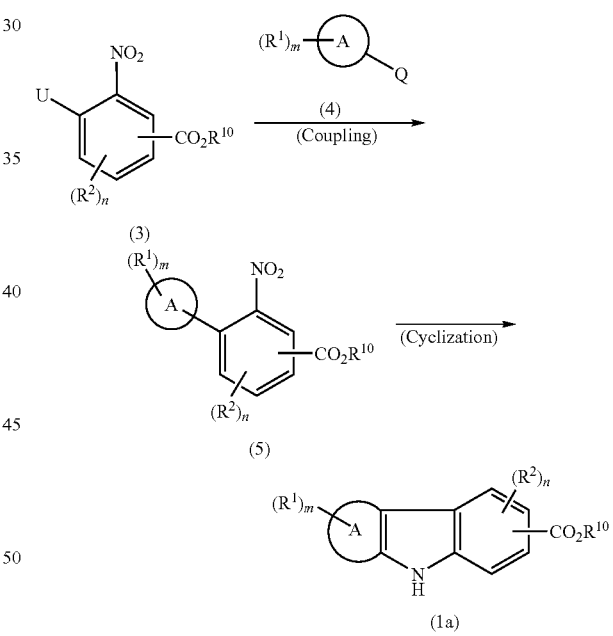

(In the formulae, either one of Q and U is —Br, —Cl, —I or —O—$SO_2$—$CF_3$ and the other represents —B(OH)$_2$ or B(O-lower alkyl)$_2$. $R^{10}$ represents a protective group such as lower alkyl or benzyl or the like. The same shall apply hereinafter.)

Among the starting compounds represented by the formula (I), a compound (1a) in which X is NH and Y is a single bond can be produced by the above reaction pathway.

In this case, the coupling reaction can be carried out by the method described in "Synthetic Communications", (England), 1981, vol. 11, p. 513-519, "Synlett", (Germany), 2000, vol. 6, p. 829-831, or "Chemistry Letters", 1989, p. 1405-1408. The cyclization reaction can be carried out at room temperature to under heating in a solvent such as benzene, toluene or the like or without solvent, using triethyl phosphite, triphenylphosphine or the like.

(Starting Material Synthesis 2)

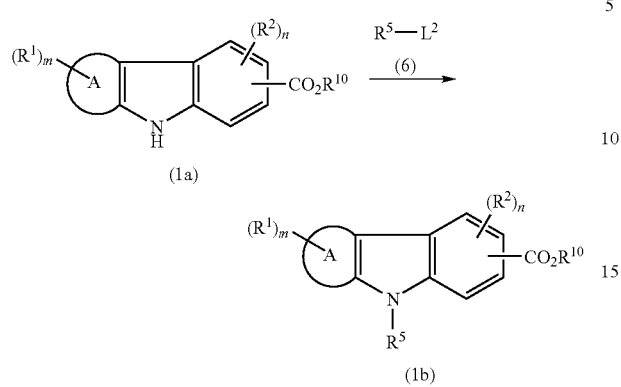

(L² represents —OH or a leaving group such as halogen, —O-methanesulfonyl, —O-p-toluenesulfonyl or the like.)

Among the starting compounds (1), a compound (1b) in which X is NR⁵ and Y is a single bond can be produced from the compound (1a) by the reaction such as alkylation, acylation, sulfonylation or the like.

When a compound (6) in which L² is a leaving group is used, the alkylation reaction can be carried out in the presence of a base such as sodium hydride, potassium hydride, potassium tert-butoxide or the like. Also, when a compound (6) in which L² is —OH is used, it can be carried out using the usual method of Mitsunobu reaction, for example, in accordance with the method described in *Tetrahedron Letters*, (Netherlands), 2002, vol. 43, p. 2187.

Regarding the acylation or sulfonylation, the reaction can be carried out using an acid halide in which the leaving group of L² is halogen, or the like, as the compound (6), in the presence of a base such as potassium hydride, potassium tert-butoxide or the like.

(Starting Material Synthesis 3)

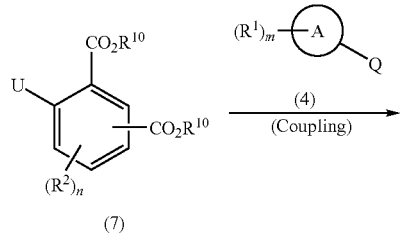

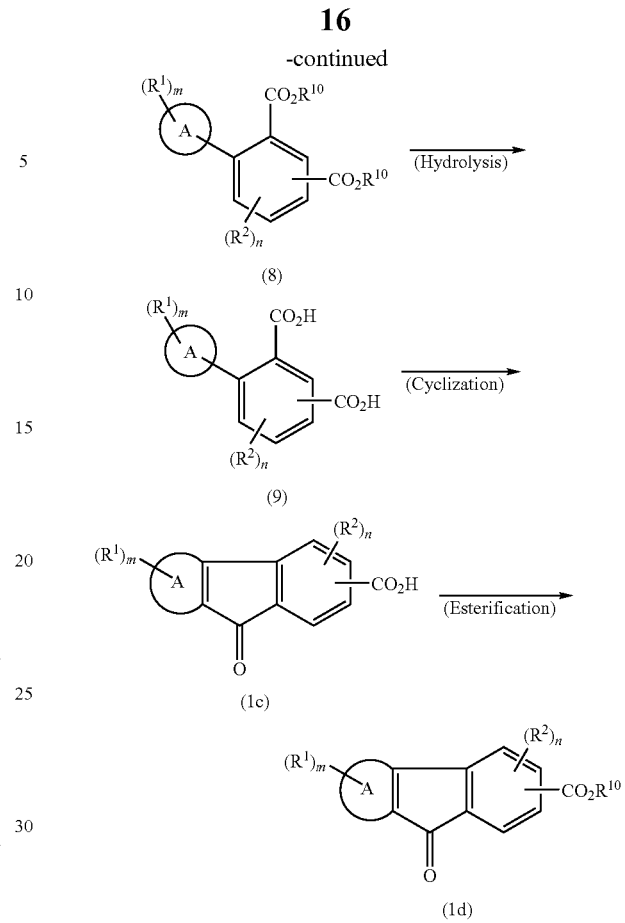

Among the starting compounds represented by the formula (1), compounds (1c) and (1d) in which —CR³R⁴ is represented by —C(O)— can be produced by the above reaction pathway. The coupling reaction can be carried out in the same manner as the coupling reaction of the starting material synthesis 1. The hydrolysis and esterification can be carried out in accordance with the hydrolysis reaction and esterification reaction described in the aforementioned "Protective Groups in Organic Synthesis". The usual method of intramolecular Friedel-Crafts' reaction can be used for the cyclization reaction and, for example, the method described in "Journal of the American Chemical Society", (USA), 1941, vol. 63, p. 1948 may be cited.

(Starting Material Synthesis 4)

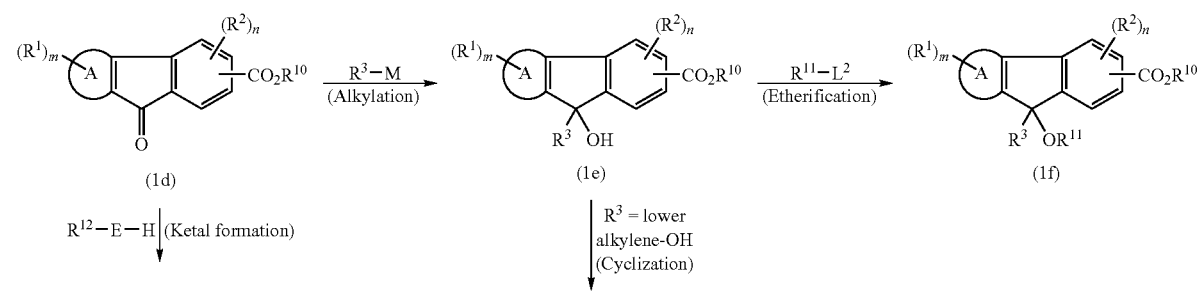

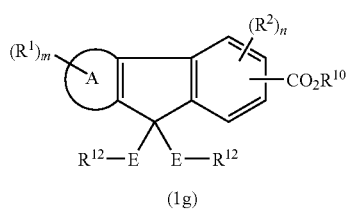

(1g)

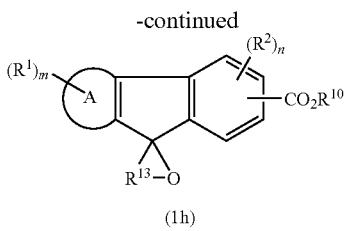

(1h)

(In the formulae, $R^{11}$ represents lower alkyl, $R^{12}$ represents lower alkyl or two $R^{12}$ together form lower alkylene, M represents the counter cation such as lithium ion, magnesium ion or the like of an organic metal reagent, E represents O or S, and $R^{13}$ represents lower alkylene.)

Among the starting compounds (1), compounds (1e) to (1h) in which at least one of $R^3$ and $R^4$ has various types of substituent can be easily produced using each reaction of the alkylation, etherification, ketal formation and cyclization or a combination thereof.

The alkylation can be carried out using an organic metal reagent such as the Grignard reagent, an organic lithium reagent, an organic cerium reagent, or the like. The etherification is carried out using an alkylating agent in which $L^2$ is a leaving group, in the presence of a base such as sodium hydride, potassium hydride, potassium tert-butoxide, silver oxide or the like. There is a case in which this is carried out under an acidic condition using a compound wherein $L^2$ is —OH, which is carried out using an acid catalyst such as hydrochloric acid, sulfuric acid, p-toluenesulfonic acid or the like, a Lewis acid such as iron nitrate or iron perchlorate or the like, in a solvent such as methanol, ethanol, benzene, toluene, xylene or the like, and at room temperature to under heating.

The ketal formation can be carried out using an acid catalyst such as hydrochloric acid, sulfuric acid, p-toluenesulfonic acid or the like and a Lewis acid such as boron trifluoride diethyl ether or the like, at room temperature to under heating.

The cyclization is carried out using an acid catalyst such as hydrochloric acid, sulfuric acid, p-toluenesulfonic acid or the like, a Lewis acid such as iron nitrate or iron perchlorate or the like, in a solvent such as benzene, toluene, xylene or the like, and at from room temperature to under heating. Alternatively, this can be carried out in the presence of a base such as sodium hydride, potassium hydride, potassium tert-butoxide, silver oxide or the like, after converting the hydroxyl group of $R^3$ into a leaving group such as halogen, sulfonic acid ester or the like.

Respective products of the above production methods can be introduced into corresponding carboxyl compounds by the deprotection of —$CO_2R^{10}$ group. For example, the deprotection reaction described in the aforementioned "Protective Groups in Organic Synthesis" can be used.

(Starting Material Synthesis 5)

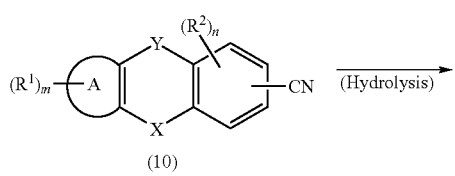

(10)

(Hydrolysis)

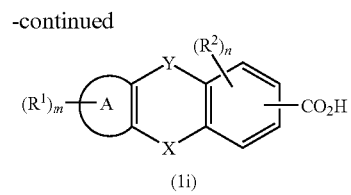

(1i)

The starting compound (1i) can be produced also by the hydrolysis of a compound (10) which has a cyano group. The compound (10) can be produced by a conventionally known method or by similar methods of the production methods of the starting material syntheses 1 to 4, using a corresponding starting material in which the —$CO_2R^{10}$ group is changed to a cyano group. The hydrolysis can be carried out at room temperature to under heating in a solvent which is inert to the reaction, such as acetic acid, water or the like, using an acid such as hydrochloric acid, sulfuric acid or the like. In addition, the reaction can also be carried out at room temperature to under heating in solvent such as an alcohol (e.g., ethanol or the like), water or the like, using a base such as potassium hydroxide or the like.

The compound (I) produced in this manner is isolated and purified as such or after making it into a salt by carrying out a salt formation treatment by a general method. The isolation and purification are carried out by employing general chemical operations such as extraction, concentration, evaporation, crystallization, filtration, recrystallization, various types of chromatography and the like.

Various isomers can be isolated by usual methods making use of the difference in a physicochemical property between isomers. For example, optical isomers can be respectively separated and purified by a method in which a racemic compound is derived into a diastereomer salt with an optically active organic acid (tartaric acid or the like) and then subjected to fractional recrystallization, or a technique such as a chiral filler-aided column chromatography or the like. In addition, an optically active compound can also be produced using an appropriate optically active compound as the starting material. In this connection, a diastereomer mixture can also be separated by a fractional crystallization, a chromatography or the like.

The reaction products obtained by the respective production methods described in the above can be isolated and purified as free compounds, salts thereof or their various solvates (e.g., hydrates and the like). The salts can be produced by subjecting to general salt formation treatment.

The isolation and purification are carried out by employing general chemical operations such as extraction, concentration, evaporation, crystallization, filtration, recrystallization, various types of chromatography and the like.

Various isomers can be isolated by usual methods making use of the difference in a physicochemical property between isomers. For example, optical isomers can be separated by a general optical resolution method such as a fractional crystallization, a chromatography or the like. In addition, an optically active isomer can also be produced from an appropriate optically active starting compound.

The pharmaceutical preparation which comprises one or two or more of the compound of the present invention or a salt thereof as the active ingredient can be prepared using carriers, fillers and other additive agents which are generally used in the preparation of medicines.

The administration may be either embodiment of oral administration by tablets, pills, capsules, granules, powders, solutions and the like, or parenteral administration by injections (e.g., intravenous, intramuscular and the like), suppositories, percutaneous preparations, transnasal preparations, inhalations and the like. The dose is optionally decided in response to each case by taking symptom, age, sex and the like of the object to be administered into consideration, but in the case of oral administration, it is generally approximately from 0.001 mg/kg to 100 mg/kg per day per adult, and this is administered once or by dividing into 2 to 4 times. Also, when intravenously administered, it is generally administered once to two or more times a day within the range of from 0.0001 mg/kg to 10 mg/kg per day per adult. Also, in the case of transnasal administration, it is generally administered once to two or more times a day within the range of from 0.0001 mg/kg to 10 mg/kg per day per adult. In addition, in the case of inhalation, it is generally administered once to two or more times a day within the range of from 0.0001 mg/kg to 1 mg/kg per day per adult.

As the solid composition for oral administration by the present invention, tablets, powders, granules and the like are used. In such a solid composition, one or more active substances are mixed with at least one inert filler such as lactose, mannitol, glucose, hydroxypropylcellulose, microcrystalline cellulose, starch, polyvinyl pyrrolidone, aluminum magnesium silicate or the like. In accordance with the usual way, the composition may contain inert additives such as lubricants (e.g., magnesium stearate and the like), disintegrators (e.g., carboxymethylstarch sodium and the like), solubilizing agents, and the like. As occasion demands, the tablets or pills may be coated with a sugar coating or a gastric or enteric coating.

As the liquid composition for oral administration, pharmaceutically acceptable emulsions, solutions, suspensions, syrups, elixirs and the like are included, which contain a generally used inert solvent such as purified water or ethanol. In addition to the inert solvent, this composition may contain auxiliary agents (e.g., solubilizing agents, moistening agents, suspending agents and the like), sweeteners, correctives, aromatics and antiseptics.

As the injections for parenteral administration, sterile aqueous or non-aqueous solutions, suspensions and emulsions are included. As the aqueous solvent, for example, distilled water for injection and physiological saline are included. Examples of the non-aqueous solvent include propylene glycol, polyethylene glycol, plant oils (e.g., olive oil or the like), alcohols (e.g., ethanol or the like), polysorbate 80 (the name in Pharmacopeia), and the like. Such a composition may further contain tonicity agents, antiseptics, moistening agents, emulsifying agents, dispersing agents, stabilizing agents and solubilizing agents. These are sterilized by, for example, filtration through a bacteria retaining filter, formulation of bactericides or irradiation. In addition, these can also be used by producing a sterile solid compositions and dissolving or suspending them in sterile water or a sterile solvent for injection prior to use.

Inhalations, transmucosal preparations transnasal preparations and the like are used in a solid, liquid or semisolid form and can be produced in accordance with conventionally known methods. For example, excipients such as lactose, starch or the like, as well as a pH adjusting agent, an antiseptic, a surfactant, a lubricant, a stabilizer, a thickener and the like, may be optionally added. An appropriate device for inhalation or blowing can be used for the administration. For example, using a conventionally known device such as a measured administration inhalation device or the like or a sprayer, a compound can be administered alone or as a powder of a prescribed mixture, or as a solution or suspension by a combination with a medicinally acceptable carrier. The dry powder inhaler or the like may be for single or multiple administration use, and a dry powder or a powder-containing capsule can be used. Alternatively, it may be in a form such as a pressurized aerosol spray or the like, which uses suitable gas such as chlorofluoroalkane, hydrofluoroalkane, carbon dioxide or the like.

(Test Methods)

Effects of the compound (I) of the present invention were confirmed by the following pharmacological tests.

Test Method (1) 5-$HT_{2B}$ Receptor Binding Test (i) Membrane Sample Preparation Cultured human 5-$HT_{2B}$ receptor-expressing HEK293-EBNA cells were washed with a phosphate buffer (PBS)(−). The cells were peeled off using a scraper in the presence of PBS(−), and the cells were recovered by a centrifugal treatment (1,000 rpm, 10 min, 4° C.). In the presence of 5 mM tris-hydrochloric acid (Tris-HCl) (pH 7.4) buffer, these were homogenized using a homogenizer (registered trademark: Polytron (PTA 10-TS)) and subjected to a centrifugal treatment (40,000×g, 10 min, 4° C.). In the presence of 50 mM Tris-HCl (pH 7.4) buffer, these were suspended using a glass-Teflon (registered trademark) homogenizer. By carrying out a centrifugal treatment (40,000×g, 10 min, 4° C.), these were suspended in 50 mM Tris-HCl (pH 7.4) and stored at −80° C.

(ii) Receptor Binding Test

A total volume of 500 µl containing 50 mM Tris-HCl, 4-mM-$CaCl_2$ (pH 7.4) buffer, the human 5-$HT_{2B}$ receptor expressing HEK293-EBNA cell membrane sample and a radio ligand [$^3$H] Mesulergine (3.1 TBq/mmol); was incubated at 25° C. for 1 hour. The compound was dissolved in 100% DMSO and diluted to respective concentrations. Nonspecific binding was regarded as the binding quantity in the presence of 1 µM ritanserin, and a result of subtracting the nonspecific binding quantity from the total binding quantity was regarded as the specific binding quantity. By adding 4 ml of 50 mM Tris-HCl buffer (pH 7.4), filtered under a reduced pressure trough a GF/B glass filter, and the filter was washed with the same buffer (4 ml×3). The glass filter was soaked in 5 ml of a liquid scintillator (trade name: Aquasol-2), and the radioactivity quantity was measured using a liquid scintillation counter. The compound concentration which inhibits 50% of the receptor binding, $IC_{50}$ value, was calculated by non-linear regression analysis using a statistical analysis software (registered trademark: SAS (ver. 6.11)), and the Ki value which shows affinity for the receptor was calculated using the formula of Cheng & Prussoff; $Ki=IC_{50}/(1+[L]/[Kd])$ ([L]: ligand concentration, [Kd]: dissociation constant). The results are shown in the following Table 1.

TABLE 1

| Ex | Ki (nM) |
|---|---|
| 1 | 4.6 |
| 66 | 0.26 |
| 81 | 0.83 |

TABLE 1-continued

| Ex | Ki (nM) |
|---|---|
| 83 | 1.5 |
| 84 | 1.3 |

Test Method (2) 5-HT$_7$ Receptor Binding Test
(i) Membrane Sample Preparation

Cultured human 5-HT$_7$ receptor expressing CHO cells were washed PBS(−). The cells were peeled off using a scraper in the presence of PBS(−), and the cells were recovered by a centrifugal treatment (1,000 rpm, 10 min, 4° C.). In the presence of 5 mM Tris-HCl (pH 7.4) buffer, these were homogenized using a homogenizer (registered trademark: Polytron (PTA 10-TS)) and subjected to a centrifugal treatment (40,000×g, 10 min, 4° C.). In the presence of 50 mM Tris-HCl (pH 7.4) buffer, these were suspended using a glass-Teflon (registered trademark) homogenizer. By carrying out a centrifugal treatment (40,000×g, 10 min, 4° C.), these were suspended in 50 mM Tris-HCl (pH 7.4) and stored at −80° C.
(ii) Receptor Binding Test A total volume of 500 µl containing 50 mM Tris-HCl, 4 mM CaCl$_2$ (pH 7.4) buffer, the human 5-HT$_7$ receptor expressing CHO cell membrane sample and a radio ligand [$^3$H] 5-HT (3.40 TBq/mmol) was incubated at 25° C. for 1 hour. The compound was dissolved in 100% DMSO and diluted to respective concentrations. Nonspecific binding was regarded as the binding quantity in the presence of 10 µM metergoline, and a result of subtracting the nonspecific binding quantity from the total binding quantity was regarded as the specific binding quantity. By adding 4 ml of 50 mM Tris-HCl buffer (pH 7.4), filtered under a reduced pressure trough a GF/B glass filter, and the filter was washed with the same buffer (4 ml×3). The glass filter was soaked in 5 ml of a liquid scintillator (trade name: Aquasol-2), and the radioactivity quantity was measured using a liquid scintillation counter. The compound concentration which inhibits 50% of the receptor binding, IC$_{50}$ value, was calculated by non-linear regression analysis using SAS (ver. 6.11), and the Ki value which shows affinity for the receptor was calculated using the formula of Cheng & Prussoff; Ki=IC$_{50}$/(1+[L]/[Kd]) ([L]: ligand concentration, [Kd]: dissociation constant). The results are shown in the following Table 2.

TABLE 2

| Ex | Ki (nM) |
|---|---|
| 1 | 0.64 |
| 66 | 2.6 |
| 81 | 0.78 |
| 83 | 0.99 |
| 84 | 2.5 |

Test Method (3) Affinity for Other Receptors

Affinities for 5-HT$_{1A}$, 5-HT$_{1B}$, 5-HT$_{2A}$, 5-HT$_{2C}$, 5-HT$_3$, 5-HT$_4$, 5-HT$_6$, $\alpha_1$, M$_1$ and D$_2$ receptors can be confirmed using conventionally known methods ("Journal of Neurochemistry", (England), 1986, vol. 47, p. 529-540; "Molecular Pharmacology", (USA), 1982, vol. 21, p. 301-314; "European Journal of Pharmacology", (Holland), 1985, vol. 106, p. 539-546; "The Journal of Pharmacology Experimental Therapeutics", (USA), 1992, vol. 263, p. 1127-1132; "British Journal of Pharmacology", (England), 1993, vol. 109, p. 618-624; "Molecular Pharmacology", (USA), 1993, vol. 43, p. 320-327; "Molecular Pharmacology", (USA), 1989, vol. 35, p. 324-330; "Cellular and Molecular Neurobiology", (Germany), 1988, vol. 8, p. 181-191; "European Journal of Pharmacology", (Holland), 1988, vol. 173, p. 177-182).

In this connection, affinities of the RS-127445 (2-amino-4-(4-fluoronaphth-1-yl)-6-isopropylpyrimidine); see WO 97/44326 for its production method) and SB-269970 ((R)-3-(2-(2-(4-methylpiperidine-1-yl)ethyl)pyrrolidine-1-sulfonyl)phenol; see WO 97/48681 for its production method), described in the following test method (4), are conventionally known, and regarding the RS-127445, it has been reported, for example in "British Journal of Pharmacology", (England), 1999, vol. 127, p. 1075-1082, that its pKi for 5-HT$_{2B}$ receptor is 9.5, and it is 1000 times or more 5-HT$_{2B}$ receptor-selective against 5-HT$_{1A}$, 5-HT$_{1B}$, 5-HT$_{2A}$, 5-HT$_{2C}$, 5-HT$_3$, 5-HT$_6$, 5-HT$_7$, $\alpha_1$, M$_1$, D$_2$ and the like receptors. Also, regarding the SB-269970, it has been reported, for example in "Journal of Medicinal Chemistry", (USA), 2000, vol. 43, p. 342-345, that pKi of said compound for 5-HT$_7$ receptor is 8.9, and it is 250 times or more 5-HT$_7$ receptor-selective against 5-HT$_{1A}$, 5-HT$_{1B}$, 5-HT$_{2A}$, 5-HT$_{2B}$, 5-HT$_{2C}$, 5-HT$_4$, 5-HT$_6$, $\alpha_1$, D$_2$ and the like receptors.

Test Method (4) Inhibitory Effect for Defecation at the Time of Confined Stress Loading The IBS-treating effect of the compound (I) of the present invention was evaluated using a method in which a confined stress is applied to rats and the evacuation quantity is measured (cf. "The Journal of Pharmacology Experimental Therapeutics", (USA), 1992, vol. 261, p. 297-303). This test is an animal model wherein it is known that the 5-HT$_3$ receptor antagonist as a diarrhea-predominant IBS-treating agent shows its efficacy.
Test Method An agent to be tested was administered to male Wistar rats (body weight 250 to 320 g, 10 animals for each group) and a confined stress was applied thereto 30 minutes thereafter. A confining cage (trade name: KN-468, 265 mm in width×95 mm in length×200 mm in height, Natsume Seisakusho, Tokyo) was used in the confined stress loading, and the number of feces during 1 hour after the stress loading was counted.

As shown in FIG. 1, the RS-127445 as a 5-HT$_{2B}$ receptor-selective antagonistic compound did not show the action to suppress defecation even when a dose of 10 mg/kg was orally administered (p.o.).

In addition, as shown in FIG. 2, the SB-269970 as a 5-HT$_7$ receptor-selective antagonistic compound also did not show the action to suppress defecation even at a dose of 10 mg/kg (p.o.).

On the other hand, as shown in FIG. 3, it was found that a synergistic effect can be obtained when both of the compounds RS-127445 and SB-269970 are simultaneously administered. That is, as shown in FIG. 1 and FIG. 2, RS-127445 and SB-269970 did not show the action even at 10 mg/kg (p.o.) when used each independently, but it was revealed that significant suppressing action is shown starting at a dose of 1 mg/kg (p.o.) when both compounds are simultaneously administered.

This effect was the same when the compound of the present invention which selectively possesses both of the 5-HT$_{2B}$ receptor antagonism and 5-HT$_7$ receptor antagonism was used. That is, as shown in FIG. 4, the compound of Example 84 which is described later showed an excellent suppressing action of 0.72 mg/kg (p.o.) in ED$_{50}$ (50% effective dose).

Based on the above results, being possessed of both of the 5-HT$_{2B}$ receptor antagonism and 5-HT$_7$ receptor antagonism, it can be expected that the compound of the present invention shows excellent effect to improve morbid state of IBS in comparison with one of the selective receptor antagonists.

Test Method (5) Preventive Effect in Guinea Pig Migraine Model

It has been suggested that an inflammatory protein leaked from dura mater blood vessel by 5-HT is concerned in the onset of migraine. This test system evaluates the migraine-preventive effect by measuring the amount of this leaked protein in the presence of a compound to be tested and was carried out by partially modifying the method described by Rachel A. Spokes and Vicki C. Middlefell in "European Journal of Pharmacology", (Holland), 1995, vol. 281, p. 75-79.

Hartley male guinea pigs (250 to 350 g) were anesthetized by the intraperitoneal administration (i.p.) of urethane (1.5 g/kg). By applying a simple canulation to a latent vein, 50 mg/kg of a fluorescent protein (FITC-BSA) was intravenously administered (i.v.) and, 5 minutes thereafter, physiological saline or 1 μmol/ml/kg of 5-HT was intravenously administered. Perfusion was carried out with physiological saline 15 minutes thereafter and blood was washed out. RS-127445 and SB-269970 were administered intravenously, and the compound of Example 1 orally, respectively 30 minutes before the administration of fluorescent protein. By detaching the skull, the dura mater was extracted and incubated in an Eppendorf tube at 37° C. for 16 hours in the presence of physiological saline adjusted to pH 11. By carrying out a centrifugal operation, the supernatant was dispensed into a plate. The fluorescence intensity was measured using a fluorescence plate reader (excitation wavelength 485 nm, absorption wavelength 530 nm). By weighing the dura mater weight, the fluorescence intensity per mg dura mater protein was calculated.

The values of fluorescence intensity measured at the time of the administration and non-administration of each compound are shown in FIG. 4 to FIG. 7. In each of them, the axis of abscissa shows dose of the compounds, and the axis of ordinate fluorescence strength per 1 mg dura mater blood vessel. The control shows fluorescence strength at the time of not adding 5-HT, namely the standard value.

As shown in FIG. 5, a $5-HT_{2B}$-selective antagonistic compound RS-127445 showed the leaked protein quantity-reducing action at 3 mg/kg, but did not lower it to the standard value when the dose was increased from 3 mg/kg to 10 mg/kg.

In addition, as shown in FIG. 6, a $5-HT_7$-selective antagonistic compound SB-269970 also showed the action at from 10 mg/kg, but did not lower the leaked protein quantity to the standard value when the dose was increased from this to 30 mg/kg.

On the other hand, as shown in FIG. 7, it was found that a synergistic effect can be obtained when both of the compounds RS-127445 and SB-269970 are simultaneously administered. That is, as shown in FIG. 5 and FIG. 6, it was shown that the minimum amount by which the both compounds show the maximum drug efficacy is 3 mg/kg for RS-127445 and 10 mg/kg for SB-269970, and it was revealed that the leaked protein quantity is almost completely suppressed to the standard value when both compounds are simultaneously administered at the same doses. This result shows that, when both functions of the $5-HT_{2B}$ receptor and $5-HT_7$ receptor are simultaneously inhibited, an excellent effect which cannot be obtained by the inhibition of one of the selective receptors can be obtained.

This effect was the same when the compound of the present invention which selectively possesses both of the $5-HT_{2B}$ receptor antagonism and $5-HT_7$ receptor antagonism was used. That is, as shown in FIG. 8, the compound of Example 1 which is described later almost completely suppressed the leaked protein quantity by 30 mg/kg of oral administration.

It was shown based on the above results that, being possessed of both of the $5-HT_{2B}$ receptor antagonism and $5-HT_7$ receptor antagonism, the compound of the present invention can completely suppress leaking amount the inflammatory protein. Accordingly, it was confirmed that the compound of the present invention has a possibility of effectively suppressing onset of migraine and has a superior effect to prevent migraine in comparison with one of the selective receptor antagonists.

EXAMPLES

The following illustratively describes production methods of the compounds of the present invention with reference to the production examples of the compounds of the present invention, though the present invention is not restricted by these examples. In this connection, since novel compounds are included in the starting compounds of the compounds of the present invention, production methods of these compounds are described as reference examples.

In this connection, the signs in the Reference Examples and Examples and in the tables which are described later have the following meanings (the same shall apply hereinafter).
REx: Reference Example number, Ex: Example number, No: compound number, Str: structural formula, Dat: physical data (EI: EI-MS; ESI: ESI-MS; APCI: APCI-MS; FAB: FAB-MS; NMR: δ (ppm) of characteristic peaks in DMSO-$d_6$ by $^1$H NMR), Sal: salt (Blank space or no description indicates that it is a free form, and the numeral before the acid component shows molar ratio. For example, when 2HCl is described, it means that the compound is dihydrochloride), Me: methyl, Et: ethyl, nPr: normal-propyl, cPr: cyclopropyl, iPr: isopropyl, nBu: normal-butyl, cBu: cyclobutyl, nPen: normal-pentyl, cPen: cyclopentyl, cHex: cyclohexyl, Ph: phenyl, Bn: benzyl, Ac: acetyl, Boc: tert-butoxycarbonyl, null: no substitution. The numeral before substituent indicates the substitution position, for example, 5-F indicates 5-fluoro. RSyn and Syn: production method (The numeral indicates that it was produced using a corresponding starting material similar to the case of a compound having respective number as Reference Example number or Example number).

Reference Example 1

Methyl 2-nitrobiphenyl-4-carboxylate was obtained by allowing methyl 3-nitro-4-{[(trifluoromethyl)sulfonyl]oxy}benzoate and phenyl boronic acid, potassium phosphate and tetrakistriphenylphosphine palladium to undergo the reaction in DMF under heating. FAB: 258 (M+H)$^+$.

Reference Example 2

Methyl 9H-carbazole-2-carboxylate was obtained by allowing methyl 2-nitrobiphenyl-4-carboxylate and triethyl phosphite to undergo the reaction under heating. FAB: 226 (M+H)$^+$.

Reference Example 3

Methyl 9-isopropyl-9H-carbazole-2-carboxylate was obtained by allowing methyl 9H-carbazole-2-carboxylate, 2-propanol and (tributylphospholanylidene)acetonitrile to undergo the reaction in toluene under heating. ESI: 268 (M+H)$^+$.

Reference Example 4

9-Isopropyl-9H-carbazole-2-carboxylic acid was obtained by allowing methyl 9-isopropyl-9H-carbazole-2-carboxylate

Reference Example 5

Methyl 5-bromomethyl-9-isopropyl-9H-carbazole-2-carboxylate was obtained by allowing methyl 9-isopropyl-5-methyl-9H-carbazole-2-carboxylate, N-bromosuccinimide and 2,2'-azobisisobutyronitrile to undergo the reaction in carbon tetrachloride under heating. FAB: 360, 362 (M+H)$^+$.

Reference Example 6

Methyl 5-dimethylaminomethyl-9-isopropyl-9H-carbazole-2-carboxylate was obtained by allowing methyl 5-bromomethyl-9-isopropyl-9H-carbazole-2-carboxylate, dimethylamine (2 M, methanol solution) and potassium carbonate to undergo the reaction at room temperature in THF. FAB: 325 (M+H)$^+$.

Reference Example 7

Methyl 5-acetoxymethyl-9-isopropyl-9H-carbazole-2-carboxylate was obtained by allowing methyl 5-bromomethyl-9-isopropyl-9H-carbazole-2-carboxylate and potassium acetate to undergo the reaction at room temperature in DMF. EI: 339 (M)$^+$.

Reference Example 8

Methyl 5-hydroxymethyl-9-isopropyl-9H-carbazole-2-carboxylate was obtained by allowing methyl 5-acetoxymethyl-9-isopropyl-9H-carbazole-2-carboxylate and potassium carbonate to undergo the reaction at room temperature in methanol-THF. FAB: 297 (M)$^+$.

Reference Example 9

Methyl 9-isopropyl-5-methoxymethyl-9H-carbazole-2-carboxylate was obtained by allowing methyl 5-hydroxymethyl-9-isopropyl-9H-carbazole-2-carboxylate, methyl iodide and silver oxide to undergo the reaction under heating in acetonitrile. FAB: 311 (M)$^+$.

Reference Example 10

Benzyl 9-isobutyryl-9H-carbazole-2-carboxylate was obtained by allowing benzyl 9H-carbazole-2-carboxylate and 2-methylpropionyl chloride to undergo the reaction at room temperature in DMF in the presence of sodium hydride. ESI: 372 (M+H)$^+$.

Reference Example 11

9-Isobutyryl-9H-carbazole-2-carboxylic acid was obtained by allowing benzyl 9-isobutyryl-9H-carbazole-2-carboxylate, and palladium-carbon to undergo the reaction at room temperature in ethanol-DMF in an atmosphere of hydrogen gas. ESI: 282 (M+H)$^+$.

Reference Example 12

Methyl 9-isopropyl-6-nitro-9H-carbazole-2-carboxylate was obtained by allowing methyl 9-isopropyl-9H-carbazole-2-carboxylate and concentrated nitric acid to undergo the reaction at room temperature in acetic acid. FAB: 313 (M+H)$^+$.

Reference Example 13

Methyl 5-formyl-9-isopropyl-9H-carbazole-2-carboxylate was obtained by allowing methyl 5-hydroxymethyl-9-isopropyl-9H-carbazole-2-carboxylate and manganese dioxide to undergo the reaction at room temperature in chloroform. FAB: 296 (M+H)$^+$.

Reference Example 14

9-Methyl-9H-carbazole-2-carboxylic acid was obtained by allowing methyl 9H-carbazole-2-carboxylate, methyl iodide and potassium hydroxide to undergo the reaction at room temperature in DMF. FAB: 226 (M+H)$^+$.

Reference Example 15

Ethyl 9-ethyl-9H-carbazole-2-carboxylate was obtained by allowing methyl 9H-carbazole-2-carboxylate, ethyl iodide and potassium hydroxide to undergo the reaction under heating in DMF. ESI: 268 (M+H)$^+$.

Reference Example 16a, Reference Example 16b

A mixture of 2,3,4,9-tetrahydro-1H-carbazole-7-carboxylic acid and 2,3,4,9-tetrahydro-1H-carbazole-5-carboxylic acid was obtained by allowing cyclohexanone and 3-hydrazinobenzoic acid to undergo the reaction under heating in acetic acid. By separating and purifying this mixture by a silica gel column chromatography, 2,3,4,9-tetrahydro-1H-carbazole-5-carboxylic acid [Reference Example 16a: FAB: 216 (M+H)$^+$] and 2,3,4,9-tetrahydro-1H-carbazole-7-carboxylic acid [Reference Example 16b: FAB: 216 (M+H)$^+$] were obtained.

Reference Example 17a, Reference Example 17b

By adding thionyl chloride to a methanol solution of a mixture of 2,3,4,9-tetrahydro-1H-carbazole-7-carboxylic acid and 2,3,4,9-tetrahydro-1H-carbazole-5-carboxylic acid at −10° C., followed by the reaction under heating and subsequent separation and purification by a column chromatography, methyl 2,3,4,9-tetrahydro-1H-carbazole-7-carboxylate [Reference Example 17a: ESI: 2230 (M+H)$^+$] and methyl 2,3,4,9-tetrahydro-1H-carbazole-5-carboxylate [Reference Example 17b: ESI: 230 (M+H)$^+$] were obtained.

Reference Example 18

3-{2-[1-(Ethoxycarbonyl)piperidin-4-ylidene]hydrazino}benzoic acid was obtained by allowing ethyl 4-oxopiperidine-1-carboxylate and 3-hydrazinobenzoic acid to undergo the reaction under heating in acetic acid. ESI: 306 (M+H)$^+$.

Reference Example 19

A mixture of diethyl 1,3,4,5-tetrahydro-2H-pyrido[4,3-b]indole-2,7-dicarboxylate and diethyl 1,3,4,5-tetrahydro-2H-pyrido[4,3-b]indole-2,9-dicarboxylate was obtained by allowing 3-{2-[1-(ethoxycarbonyl)piperidin-4-ylidene]hydrazino}benzoic acid and concentrated hydrochloric acid to undergo the reaction under heating in ethanol. ESI: 317 (M+H)$^+$.

Reference Example 20

A mixture of 2-(ethoxycarbonyl)-2,3,4,5-tetrahydro-1H-pyrido[4,3-b]indole-7-carboxylic acid and 2-(ethoxycarbonyl)-2,3,4,5-tetrahydro-1H-pyrido[4,3-b]indole-9-carboxylic acid was obtained by allowing a mixture of diethyl 1,3,4,5-tetrahydro-2H-pyrido[4,3-b]indole-2,7-dicarboxylate and diethyl 1,3,4,5-tetrahydro-2H-pyrido[4,3-b]indole-2,9-dicarboxylate and potassium hydroxide to undergo the reaction under heating in methanol-water. ESI: 287 (M–H)$^+$.

Reference Example 21

10H-Phenoxazine-3-carboxylic acid was obtained by allowing 10H-phenoxazine-3-carbonitrile produced in accordance with "New Journal of Chemistry", (England), 2001, vol. 25, no. 3, p. 385, and concentrated hydrochloric acid under heating in acetic acid. FAB: 227 (M)$^+$.

Reference Example 22

10-Methyl-10H-phenoxazine-3-carbonitrile was obtained by allowing 10H-phenoxazine-3-carbonitrile produced in accordance with "New Journal of Chemistry", (England), 2001, vol. 25, no. 3, p. 385, methyl iodide and sodium hydride at room temperature in THF. FAB: 223 (M+H)$^+$.

Reference Example 23

10-Methyl-10H-phenoxazine-3-carboxylic acid was obtained by treating 10-methyl-10H-phenoxazine-3-carbonitrile with 8 M potassium hydroxide aqueous solution under heating in ethanol. FAB: 241 (M)$^\pm$.

Reference Example 24

10H-Phenoxazine-2-carbonitrile was obtained by producing it in accordance with "New Journal of Chemistry", (England), 2001, vol. 25, no. 3, p. 385.

Reference Example 25

10H-Phenoxazine-2-carboxylic acid was obtained by producing it in accordance with "Journal of Organic Chemistry", 1960, vol. 25, p. 747.

Reference Example 26

Ethyl 10H-phenoxazine-2-carboxylate was obtained by producing it in accordance with "Journal of Organic Chemistry", 1960, vol. 25, p. 747.

Reference Example 27

Diethyl 4-(2-thienyl)isophthalate was obtained by allowing 4-bromophthalic acid diethyl ester, 2-thienyl boronic acid, sodium carbonate and tetrakistriphenylphosphine palladium to undergo the reaction under heating in toluene-ethanol-water. FAB: 305 (M+H)$^+$.

Reference Example 28

4-(2-Thienyl)isophthalic acid was obtained by treating an ethanol solution of diethyl 4-(2-thienyl)isophthalate with 5 M sodium hydroxide aqueous solution. FAB: 248 (M)$^+$.

Reference Example 29

4-Oxo-4H-indeno[1,2-b]thiophene-6-carboxylic acid was obtained by allowing 4-(2-thienyl)isophthalic acid and trifluoroacetic anhydride to undergo the reaction under heating in trifluoroacetic acid. FAB: 230 (M)$^-$.

Reference Example 30

Ethyl 4-oxo-4H-indeno[1,2-b]thiophene-6-carboxylate was obtained by allowing 4-oxo-4H-indeno[1,2-b]thiophene-6-carboxylic acid and concentrated sulfuric acid to undergo the reaction under heating in ethanol. EI: 258 (M)$^+$.

Reference Example 31

Ethyl spiro[1,3-dithiolan-2,4'-indeno[1,2-b]thiophene]-6'-carboxylate was obtained by allowing ethyl 4-oxo-4H-indeno[1,2-b]thiophene-6-carboxylate, 1,2-ethanedithiol and boron trifluoride diethyl ether complex to undergo the reaction under heating in acetic acid. FAB: 334 (M)$^+$.

Reference Example 32

4-Hydroxy-4-methyl-4H-indeno[1,2-b]thiophene-6-carboxylic acid was obtained by allowing 4-oxo-4H-indeno[1,2-b]thiophene-6-carboxylic acid and methylmagnesium bromide to undergo the reaction at 0° C. in THF. FAB: 245 (M–H)$^-$ Reference Example 33

Methyl 4-methoxy-4-methyl-4H-indeno[1,2-b]thiophene-6-carboxylate was obtained by allowing 4-hydroxy-4-methyl-4H-indeno[1,2-b]thiophene-6-carboxylic acid, methyl iodide and sodium hydride to undergo the reaction at room temperature in DMF. FAB: 275 (M+H)$^+$.

Reference Example 34

Methyl 4-allyl-4-hydroxy-4H-indeno[1,2-b]thiophene-6-carboxylate was obtained by allowing 4-allyl-4-hydroxy-4H-indeno[1,2-b]thiophene-6-carboxylic acid [ESI: 273 (M+H)$^+$] synthesized by carrying out the same operation of Reference Example 32 using 4-oxo-4H-indeno[1,2-b]thiophene-6-carboxylic acid and allylmagnesium bromide to undergo the reaction with methyl iodide and sodium bicarbonate at 50° C. in DMF. ESI: 287 (M+H)$^+$.

Reference Example 35

Methyl 4-hydroxy-4-(3-hydroxypropyl)-4H-indeno[1,2-b]thiophene-6-carboxylate was obtained by allowing methyl 4-allyl-4-hydroxy-4H-indeno[1,2-b]thiophene-6-carboxylate and BH$_3$-THF complex to undergo the reaction at 0° C. in THF and then further carrying out the reaction at 60° C. by adding hydrogen peroxide aqueous solution and sodium hydroxide aqueous solution thereto. ESI: 305 (M+H)$^+$.

Reference Example 36

4,5-Dihydro-3H-spiro[furan-2,4'-indeno[1,2-b]thiophene]-6'-carboxylic acid was obtained by treating, with 1 M sodium hydroxide aqueous solution, methyl 4-hydroxy-4-(3-{[(4-methylphenyl)sulfonyl]oxy}propyl)-4H-indeno[1,2-b]thiophene-6-carboxylate which had been obtained by allowing methyl 4-hydroxy-4-(3-hydroxypropyl)-4H-indeno[1,2-b]thiophene-6-carboxylate and 4-methylbenzenesulfonyl chloride to undergo the reaction at 0° C. in pyridine. ESI: 273 (M+H)$^+$.

Reference Example 37

9-Oxo-9H-indeno[2,1-c]pyridine-7-carboxylic acid was obtained by allowing 4-pyridin-4-ylphthalic acid [FAB: 244 (M+H)+] which had been synthesized by carrying out the same operations of Reference Examples 27 and 28 using 4-bromoisophthalic acid diethyl ester and 4-pyridine boronic acid to undergo the reaction with lithium 2,2,6,6-tetramethylpiperidide at 0° C. in THF. By carrying out reaction of this compound by the same method of Reference Example 30, ethyl 9-oxo-9H-indeno[2,1-c]pyridine-7-carboxylate was obtained. FAB: 254 (M+H)+.

The reference example compounds shown in Tables 3 to 10 which are described later were produced using respectively corresponding starting materials in the same manner as in the methods of Reference Examples 1 to 37 described in the above.

Example 1

A 134 mg portion of CDI was added to 4 ml DMF solution of 140 mg 9-isopropyl-9H-carbazole-2-carboxylic acid, followed by stirring at 50° C. for 1 hour. After spontaneous cooling to room temperature, 238 mg of guanidine carbonate was added thereto, followed by stirring overnight at room temperature. After evaporation of the solvent, water was added thereto and the thus precipitated solid was purified by a silica gel column chromatography (Chromatorex (registered trademark), methanol/chloroform) to obtain 157 mg of N-(diaminomethylene)-9-isopropyl-9H-carbazole-2-carboxamide as a pale yellow solid.

Example 2

A 192 mg portion of sodium hydride (60%) was added to 6.5 ml DMF solution of 573 mg guanidine hydrochloride and stirred at room temperature for 1 hour. A 6.5 ml DMF solution of 270 mg methyl 9H-carbazole-2-carboxylate was added to this solution, followed by stirring at 70° C. for 2.5 hours. After spontaneous cooling to room temperature and subsequent evaporation of the solvent, water was added thereto and the thus precipitated solid was purified by Chromatorex (methanol/chloroform) to obtain 236 mg of N-(diaminomethylene)-9H-carbazole-2-carboxamide as a pale yellow solid.

Example 3

A 1.26 ml portion of 1 M hydrochloric acid and 30 mg of 20% palladium hydroxide were added to 9 ml ethanol solution of 300 mg N-(diaminomethylene)-9-[1-(diphenylmethyl)-azetidin-3-yl]-9H-carbazole-2-carboxamide, followed by stirring at room temperature for 4 days under an atmosphere of hydrogen gas. After carrying out celite filtration after adding 1 M sodium hydroxide aqueous solution, the solvent was evaporated, followed by purification by Chromatorex (methanol/chloroform) to obtain 89 mg of 9-azetidin-3-yl-N-(diaminomethylene)-9H-carbazole-2-carboxamide.

Example 4

A 1.0 ml portion of 1 M hydrochloric acid and 40 mg of 10% palladium-carbon were added to an ethanol 9 ml-THF 3 ml solution of 393 mg N-(diaminomethylene)-9-[2-(benzyloxy)ethyl]-9H-carbazole-2-carboxamide, followed by stirring at room temperature for 3 days under an atmosphere of hydrogen gas. After carrying out celite filtration by adding 1 M sodium hydroxide aqueous solution, the organic solvent was evaporated and the water layer was extracted with chloroform, followed by washing with saturated brine and drying with anhydrous magnesium sulfate. By evaporating the solvent, 140 mg of N-(diaminomethylene)-9-(2-hydroxyethyl)-9H-carbazole-2-carboxamide was obtained.

Example 5

A 20 mg portion of 10% palladium-carbon was added to an ethanol 5 ml-THF 3 ml solution of 106 mg N-(diaminomethylene)-9-isopropyl-6-nitro-9H-carbazole-2-carboxamide, followed by stirring at room temperature for 4 hours under an atmosphere of hydrogen gas. After carrying out Celite filtration, the solvent was evaporated to obtain 128 mg of 6-amino-N-(diaminomethylene)-9-isopropyl-9H-carbazole-2-carboxamide.

Example 6

A 0.6 ml portion of 4 M hydrogen chloride/ethyl acetate was added to 4.4 ml ethanol solution of 201 mg tert-butyl 4-(2-{[(diaminomethylene)amino]carbonyl}-9H-carbazol-9-yl)piperidine-1-carboxylate which had been synthesized in the same manner as in Example 1, followed by stirring overnight at room temperature. The thus precipitated-solid was collected by filtration and washed with EtOH to obtain 125 mg of N-(diaminomethylene)-9-piperidin-4-yl-9H-carbazole-2-carboxamide dihydrochloride as pale yellow solid.

Example 7

A 156 mg portion of sodium borohydride was added to a 10 ml methanol suspension of 280 mg N-(diaminomethylene)-8-oxo-8H-indeno[2,1-b]thiophene-6-carboxamide, followed by stirring at room temperature for 30 minutes. After evaporation of the solvent, the solid precipitated by adding water was purified by Chromatorex (DMF/chloroform) to obtain 284 mg of N-(diaminomethylene)-8-hydroxy-8H-indeno[2,1-b]thiophene-6-carboxamide as a pale green solid.

The Example compounds shown in Tables 11 to 19 which are described later were produced using respectively corresponding starting materials (except that Example 61 used a starting material in which the hydroxyl group was protected with acetyl group) in the same manner as in the methods of Examples 1 to 7 described in the above.

In addition, structures of other compounds of the present invention are shown in Tables 20 to 24. These can be easily synthesized using the aforementioned production methods, the methods described in examples and the methods obvious to those skilled in the art, or modified methods thereof.

TABLE 3

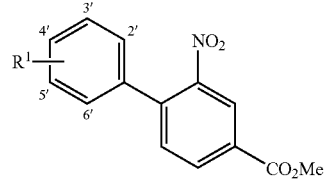

| REx | RSyn | R¹ | Dat |
|---|---|---|---|
| 38 | 1 | 2'-F | FAB: 275 (M)+ |
| 39 | 1 | 3'-F | FAB: 276 (M + H)+ |
| 40 | 1 | 4'-F | FAB: 276 (M + H)+ |
| 41 | 1 | 2'-Me | FAB: 272 (M + H)+ |
| 42 | 1 | 3'-Me | FAB: 272 (M + H)+ |

TABLE 3-continued

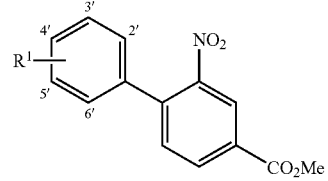

| REx | RSyn | R[1] | Dat |
|---|---|---|---|
| 43 | 1 | 4'-Me | FAB: 272 (M + H)+ |
| 44 | 1 | 2'-OMe | FAB: 288 (M + H)+ |
| 45 | 1 | 3'-OMe | FAB: 288 (M + H)+ |
| 46 | 1 | 4'-OMe | FAB: 288 (M + H)+ |
| 47 | 1 | 2'-Cl | FAB: 292 (M + H)+ |
| 48 | 1 | 3'-Cl | FAB: 291 (M)+ |
| 49 | 1 | 4'-Cl | FAB: 292 (M + H)+ |
| 50 | 1 | 2'-CN | ESI: 283 (M + H)+ |
| 51 | 1 | 3'-CN | FAB: 283 (M + H)+ |
| 52 | 1 | 4'-CN | FAB: 283 (M + H)+ |

TABLE 4

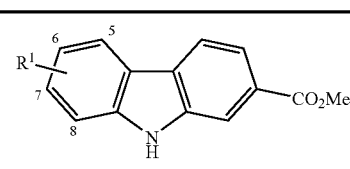

| REx | RSyn | R[1] | Dat |
|---|---|---|---|
| 53 | 2 | 5-F | FAB: 244 (M + H)+ |
| 54 | 2 | 6-F | FAB: 244 (M + H)+ |
| 55 | 2 | 7-F | FAB: 244 (M + H)+ |
| 56 | 2 | 8-F | FAB: 244 (M + H)+ |
| 57 | 2 | 5-Me | FAB: 240 (M + H)+ |
| 58 | 2 | 6-Me | FAB: 240 (M + H)+ |
| 59 | 2 | 7-Me | FAB: 240 (M + H)+ |
| 60 | 2 | 8-Me | FAB: 240 (M + H)+ |
| 61 | 2 | 5-OMe | FAB: 256 (M + H)+ |
| 62 | 2 | 6-OMe | FAB: 255 (M)+ |
| 63 | 2 | 7-OMe | FAB: 256 (M + H)+ |
| 64 | 2 | 8-OMe | FAB: 256 (M + H)+ |
| 65 | 2 | 5-Cl | FAB: 259 (M)+ |
| 66 | 2 | 6-Cl | FAB: 260 (M + H)+ |
| 67 | 2 | 7-Cl | FAB: 260 (M + H)+ |
| 68 | 2 | 8-Cl | FAB: 260 (M + H)+ |
| 69 | 2 | 5-CN | FAB: 249 (M − H)− |
| 70 | 2 | 6-CN | ESI: 249 (M − H)− |
| 71 | 2 | 7-CN | ESI: 249 (M − H)− |
| 72 | 2 | 8-CN | ESI: 249 (M − H)− |

TABLE 5

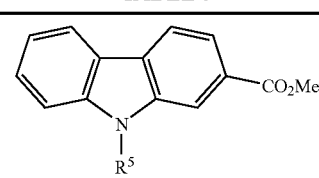

| REx | RSyn | R[5] | Dat |
|---|---|---|---|
| 73 | 3 | nPr | ESI: 268 (M + H)+ |
| 74 | 3 | nBu | ESI: 282 (M + H)+ |
| 75 | 3 | nPen | ESI: 296 (M + H)+ |
| 76 | 3 | —(CH$_2$)$_2$OMe | ESI: 284 (M + H)+ |
| 77 | 3 | —(CH$_2$)$_2$OBn | ESI: 360 (M + H)+ |
| 78 | 3 | —(CH$_2$)$_2$NMe$_2$ | ESI: 297 (M + H)+ |
| 79 | 3 | —(CH$_2$)$_3$OMe | FAB: 297 (M)+ |
| 80 | 3 | —(CH$_2$)$_2$Ph | FAB: 330 (M + H)+ |

TABLE 5-continued

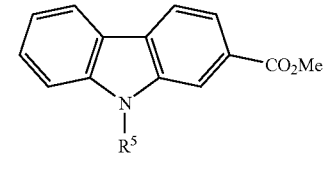

| REx | RSyn | R[5] | Dat |
|---|---|---|---|
| 81 | 3 | Bn | ESI: 316 (M + H)+ |
| 82 | 3 | cBu | ESI: 280 (M + H)+ |
| 83 | 3 | cPen | ESI: 294 (M + H)+ |
| 84 | 3 | cHex | ESI: 308 (M + H)+ |
| 85 | 3 | —CH(C$_2$H$_5$)$_2$ | ESI: 296 (M + H)+ |
| 86 | 3 | piperidine-N-Boc | FAB: 408 (M)+ |
| 87 | 3 | tetrahydropyran-4-yl | EI: 309 (M)+ |
| 88 | 3 | —CH$_2$-cPr | ESI: 280 (M + H)+ |
| 89 | 3 | 3-methyl-3-ethyloxetanyl | APCI: 310 (M + H)+ |
| 90 | 3 | 2-furylmethyl | ESI: 306 (M + H)+ |
| 91 | 3 | 3-methyl-1-(diphenylmethyl)azetidinyl | ESI: 447 (M + H)+ |
| 92 | 3 | 3-furylmethyl | ESI: 306 (M + H)+ |
| 93 | 3 | tetrahydropyran-4-ylmethyl | FAB: 323 (M)+ |
| 94 | 10 | N-acetylmorpholinyl | FAB: 339 (M + H)+ |

TABLE 6

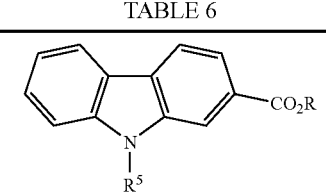

| REx | RSyn | R[5] | R | Dat |
|---|---|---|---|---|
| 95 | 3 | Et | Et | ESI: 268 (M + H)+ |
| 96 | 3 | oxiranylmethyl | Bn | EI: 357 (M)+ |

TABLE 6-continued

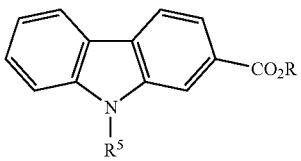

| REx | RSyn | R⁵ | R | Dat |
|---|---|---|---|---|
| 97 | 10 | Ac | Bn | ESI: 344 (M + H)⁺ |
| 98 | 10 | —S(O)₂-Me | Bn | EI: 379 (M)⁺ |
| 99 | 10 | —S(O)₂-iPr | Bn | ESI: 408 (M + H)⁺ |
| 100 | 10 | —C(O)NMe₂ | Bn | FAB: 373 (M + H)⁺ |

TABLE 7

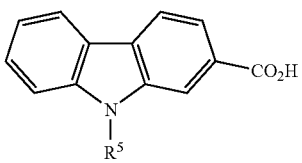

| REx | RSyn | R⁵ | Dat |
|---|---|---|---|
| 101 | 4 | nPr | ESI: 252 (M − H)⁻ |
| 102 | 4 | nBu | ESI: 266 (M − H)⁻ |
| 103 | 4 | nPen | ESI: 280 (M − H)⁻ |
| 104 | 4 | —(CH₂)₂OBn | ESI: 344 (M − H)⁻ |
| 105 | 4 | —(CH₂)₃OMe | ESI: 282 (M − H)⁻ |
| 106 | 4 | Bn | ESI: 300 (M − H)⁻ |
| 107 | 4 | —(CH₂)₂Ph | ESI: 314 (M − H)⁻ |
| 108 | 4 | cBu | FAB: 266 (M + H)⁺ |
| 109 | 4 | cPen | ESI: 278 (M − H)⁻ |
| 110 | 4 | cHex | ESI: 292 (M − H)⁻ |
| 111 | 4 | —CH(C₂H₅)₂ | ESI: 280 (M − H)⁻ |
| 112 | 4 | (tetrahydropyran-4-yl) | ESI: 294 (M − H)⁻ |
| 113 | 4 | (1-Boc-piperidin-4-yl) | ESI: 393 (M − H)⁻ |
| 114 | 4 | —CH₂-cPr | ESI: 264 (M − H)⁻ |
| 115 | 4 | (furan-2-yl-CH₂CH₂) | ESI: 290 (M − H)⁻ |
| 116 | 4 | (furan-3-yl-CH₂CH₂) | ESI: 290 (M − H)⁻ |
| 117 | 4 | (tetrahydropyran-4-yl-CH₂CH₂) | ESI: 308 (M − H)⁻ |
| 118 | 4 | (4-acetylmorpholin-2-yl) | FAB: 325 (M + H)⁺ |
| 119 | 11 | (oxiranyl-CH₂CH₂) | ESI: 266 (M − H)⁻ |
| 120 | 11 | Ac | ESI: 254 (M + H)⁻ |
| 121 | 11 | —S(O)₂-Me | FAB: 289 (M)⁺ |

TABLE 7-continued

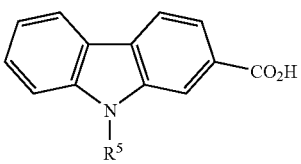

| REx | RSyn | R⁵ | Dat |
|---|---|---|---|
| 122 | 11 | —S(O)₂-iPr | ESI: 316 (M − H)⁻ |
| 123 | 11 | —C(O)NMe₂ | FAB: 283 (M + H)⁺ |

TABLE 8

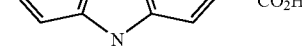

| REx | RSyn | R¹ | R | Dat |
|---|---|---|---|---|
| 124 | 3 | 5-F | Me | FAB: 286 (M + H)⁺ |
| 125 | 3 | 6-F | Me | FAB: 286 (M + H)⁺ |
| 126 | 3 | 7-F | Me | FAB: 286 (M + H)⁺ |
| 127 | 3 | 8-F | Me | FAB: 286 (M + H)⁺ |
| 128 | 3 | 5-Me | Me | FAB: 282 (M + H)⁺ |
| 129 | 3 | 6-Me | Me | FAB: 282 (M + H)⁺ |
| 130 | 3 | 7-Me | Me | FAB: 282 (M + H)⁺ |
| 131 | 3 | 8-Me | Me | FAB: 282 (M + H)⁺ |
| 132 | 3 | 5-OMe | Me | FAB: 298 (M + H)⁺ |
| 133 | 3 | 6-OMe | Me | FAB: 297 (M)⁺ |
| 134 | 3 | 7-OMe | Me | FAB: 298 (M + H)⁺ |
| 135 | 3 | 8-OMe | Me | FAB: 298 (M + H)⁺ |
| 136 | 3 | 6-Cl | Me | FAB: 302 (M + H)⁺ |
| 137 | 3 | 5-Cl | Me | ESI: 302 (M + H)⁺ |
| 138 | 3 | 7-Cl | Me | ESI: 302 (M + H)⁺ |
| 139 | 3 | 8-Cl | Me | FAB: 302 (M + H)⁺ |
| 140 | 3 | 5-CN | Me | FAB: 293 (M + H)⁺ |
| 141 | 3 | 6-CN | Me | FAB: 293 (M + H)⁺ |
| 142 | 3 | 7-CN | Me | FAB: 293 (M + H)⁺ |
| 143 | 3 | 8-CN | Me | FAB: 293 (M + H)⁺ |
| 144 | 4 | 5-CN | H | FAB: 279 (M + H)⁺ |
| 145 | 4 | 6-CN | H | FAB: 277 (M − H)⁻ |
| 146 | 4 | 7-CN | H | FAB: 279 (M + H)⁺ |
| 147 | 4 | 8-CN | H | FAB: 279 (M + H)⁺ |
| 148 | 4 | 6-NO₂ | H | FAB: 297 (M − H)⁻ |
| 149 | 4 | 5-C(O)H | H | FAB: 282 (M + H)⁺ |

TABLE 9

| REx | RSyn | Str | Dat |
|---|---|---|---|
| 150 | 27 |  | FAB: 305 (M + H)⁺ |

TABLE 9-continued

| REx | RSyn | Str | Dat |
|---|---|---|---|
| 151 | 28 | (structure) | FAB: 247 (M − H)− |
| 152 | 29 | (structure) | FAB: 231 (M + H)+ |
| 153 | 4 | (structure) | FAB: 305 (M − H)− |
| 154 | 4 | (structure) | FAB: 259 (M − H)− |
| 155 | 27 | (structure) | FAB: 300 (M + H)+ |
| 156 | 4 | (structure) | ESI: 226 (M + H)+ |

TABLE 10

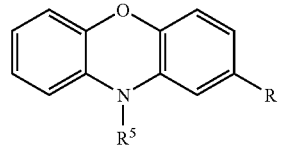

| REx | RSyn | $R^5$ | R | Dat |
|---|---|---|---|---|
| 157 | 3 | (4-methyltetrahydropyran) | $CO_2Et$ | ESI: 340 (M + H)+ |
| 158 | 3 | —$(CH_2)_2$—$NMe_2$ | $CO_2Et$ | ESI: 327 (M + H)+ |
| 159 | 3 | (3-ethyl-3-methyloxetane) | $CO_2Et$ | ESI: 340 (M + H)+ |
| 160 | 3 | Et | $CO_2Et$ | APCI: 283 (M)+ |
| 161 | 3 | cBu | $CO_2Et$ | ESI: 310 (M + H)+ |
| 162 | 4 | Et | $CO_2H$ | ESI: 254 (M − H)− |
| 163 | 4 | cBu | $CO_2H$ | ESI: 280 (M − H)− |
| 164 | 22 | Me | CN | FAB: 222 (M)+ |
| 165 | 23 | Me | $CO_2H$ | FAB: 241 (M)+ |

TABLE 11

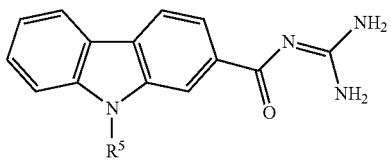

| Ex | Syn | $R^5$ | Sal | Dat |
|---|---|---|---|---|
| 1 | 1 | iPr | HCl | NMR: 1.69 (6H, d, J = 6.9 Hz), 5.31 (1H, sept, J = 6.9 Hz), 8.65 (1H, s).; FAB: 295 (M + H)+ |
| 2 | 2 | H | HCl | NMR: 7.24 (1H, dt, J = 7.3, 1.0 Hz), 7.51 (1H, dt, J = 7.3, 1.0 Hz), 8.33 (1H, s).; FAB: 253 (M + H)+ |
| 3 | 3 | (3-methylazetidine) | 2HCl | NMR: 4.52 (2H, dd, J = 8.3, 8.3 Hz), 4.99 (2H, dd, J = 8.3, 8.3 Hz), 8.76 (1H, s).; FAB: 308 (M + H)+ |
| 4 | 4 | —$(CH_2)_2OH$ | HCl | NMR: 3.84 (2H, t, J = 5.4 Hz), 4.58 (2H, t, J = 5.4 Hz), 8.67 (1H, s).; FAB: 297 (M + H)+ |
| 8 | 1 | Me | HCl | NMR: 4.01 (3H, s), 7.29 (1H, dt, J = 7.3, 1.0 Hz), 8.71 (1H, d, J = 1.5 Hz).; FAB: 267 (M + H)+ |
| 9 | 2 | Et | HCl | NMR: 1.37 (3H, t, J = 7.3 Hz), 4.59 (2H, q, J = 7.3 Hz), 8.72 (1H, d, J = 1.5 Hz).; FAB: 281 (M + H)+ |
| 10 | 1 | nPr | HCl | NMR: 0.92 (3H, t, J = 7.3 Hz), 1.86 (2H, tq, J = 7.3, 7.3 Hz), 8.78 (1H, s).; FAB: 295 (M + H)+ |
| 11 | 1 | nBu | HCl | NMR: 0.89 (3H, t, J = 7.3 Hz), 1.35 (2H, tq, J = 7.4, 7.3 Hz), 8.74 (1H, d, J = 1.5 Hz).; FAB: 309 (M + H)+ |

TABLE 11-continued

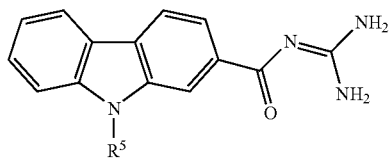

| Ex | Syn | R⁵ | Sal | Dat |
|---|---|---|---|---|
| 12 | 1 | nPen | HCl | NMR: 0.81 (3H, t, J = 6.8 Hz), 1.82 (2H, tt, J = 7.4, 6.8 Hz), 8.70 (1H, d, J = 1.5 Hz).; FAB: 323 (M + H)⁺ |
| 13 | 1 | —CH(Et)₂ | HCl | NMR: 0.66 (6H, t, J = 6.4 Hz), 4.60-5.00 (1H, m), 8.89 (1H, s).; ESI: 323 (M + H)⁺ |
| 14 | 2 | —(CH₂)₂OMe | HCl | NMR: 3.18 (3H, s), 4.69 (2H, t, J = 5.2 Hz), 8.58 (1H, s).; ESI: 311 (M + H)⁺ |
| 15 | 1 | —(CH₂)₂OBn | HCl | NMR: 3.90 (2H, t, J = 4.9 Hz), 4.45 (2H, s), 8.84 (1H, s).; FAB: 387 (M + H)⁺ |
| 16 | 1 | —(CH₂)₃OMe | HCl | NMR: 2.07 (2H, tt, J = 6.9, 6.3 Hz), 3.20 (3H, s), 8.65 (1H, d, J = 0.9 Hz).; FAB: 325 (M + H)⁺ |
| 17 | 2 | —(CH₂)₂N(Me)₂ | 2HCl | NMR: 2.97 (6H, s), 4.96 (2H, brt, J = 7.8 Hz), 8.83 (1H, s).; FAB: 324 (M + H)⁺ |
| 18 | 1 | cBu | HCl | NMR: 1.92-2.00 (1H, m), 5.49 (1H, quint, J = 8.8 Hz), 8.57 (1H, d, J = 1.6 Hz).; ESI: 307 (M + H)⁺ |
| 19 | 1 | cPen | HCl | NMR: 1.76-1.88 (2H, m), 5.47 (1H, quint, J = 9.0 Hz), 8.58 (1H, s).; FAB: 321 (M + H)+ |
| 20 | 1 | cHex | HCl | NMR: 1.64-1.77 (4H, m), 1.84-1.93 (4H, m), 8.80 (1H, s).; FAB: 335 (M + H)+ |

TABLE 12

| 21 | 1 | 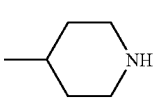 | HCl | NMR: 1.82 (2H, brd, J = 11.5 Hz), 4.09 (2H, brdd, J = 11.5, 2.0 Hz), 8.65-8.88 (3H, m).; FAB: 337 (M + H)+ |
|---|---|---|---|---|
| 6 | 6 | 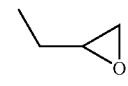 | 2HCl | NMR: 2.01 (2H, brd, J = 11.2 Hz), 5.33-5.43 (1H, m), 8.99 (1H, s).; FAB: 336 (M + H)⁺ |
| 22 | 1 | Ac | HCl | NMR: 3.00 (3H, s), 8.40 (1H, d, J = 8.3 Hz), 8.93 (1H, d, J = 0.9 Hz).; FAB: 295 (M + H)⁺ |
| 23 | 1 | —C(O)-iPr | HCl | NMR: 1.35 (6H, d, J = 6.3 Hz), 3.88 (1H, sept, J = 6.3 Hz), 8.94 (1H, s).; FAB: 323 (M + H)⁺ |
| 24 | 1 | —S(O)₂-iPr | HCl | NMR: 1.20 (6H, d, J = 6.8 Hz), 4.10 (1H, sept, J = 6.8 Hz), 8.69 (1H, d, J = 1.4 Hz).; FAB: 359 (M + H)⁺ |
| 25 | 1 | —C(O)—NMe₂ | HCl | NMR: 3.09 (6H, s), 7.38-7.43 (1H, m), 8.37 (1H, s).; FAB: 324 (M + H)⁺ |
| 26 | 1 | 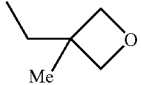 | HCl | NMR: 3.78 (1H, dd, J = 5.9, 11.2 Hz), 3.85 (1H, dd, J = 11.2, 3.9 Hz), 8.74 (1H, s).; EI: 308 (M)⁺ |
| 27 | 2 | 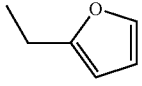 | | NMR: 1.34 (3H, s), 4.54 (2H, s), 8.27 (1H, s).; FAB: 337 (M + H)⁺ |
| 28 | 1 | —CH₂-cPr | HCl | NMR: 0.43-0.47 (2H, m), 4.48 (2H, d, J = 7.3 Hz), 8.79 (1H, d, J = 1.5 Hz).; FAB: 307 (M + H)⁺ |
| 29 | 1 | 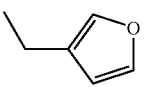 | HCl | NMR: 5.80 (2H, s), 6.37 (1H, dd, J = 3.4, 2.0 Hz), 8.91 (1H, s).; FAB: 333 (M + H)⁺ |
| 30 | 1 | | HCl | NMR: 5.62 (2H, s), 6.37 (1H, d, J = 1.5 Hz), 8.90 (1H, d, J = 1.4 Hz).; FAB: 333 (M + H)⁺ |
| 31 | 1 | —CH₂CH₂Ph | HCl | NMR: 3.13 (2H, t, J = 7.3 Hz), 4.74 (2H, t, J = 7.3 Hz), 8.67 (1H, d, J = 1.0 Hz).; FAB: 357 (M + H)⁺ |

TABLE 12-continued

| | | | | |
|---|---|---|---|---|
| 32 | 1 | 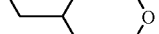 | HCl | NMR: 3.18 (2H, dd, J = 11.7, 11.7 Hz), 3.79 (2H, dd, J = 11.7, 2.4 Hz), 8.84 (1H, d, J = 0.9 Hz).; FAB: 351 (M + H)+ |
| 33 | 1 | Bn | HCl | NMR: 5.83 (2H, s), 8.40 (1H, d, J = 8.3 Hz), 8.77 (1H, s).; FAB: 343 (M + H)+ |
| 34 | 1 | —S(O)₂-Me | HCl | NMR: 3.29 (3H, s), 7.48 (1H, t, J = 7.8 Hz), 8.79 (1H, s).; FAB: 331 (M + H)+ |
| 35 | 2 | 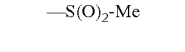 | | NMR: 4.76 (1H, s), 5.45-5.48 (1H, m), 8.73 (1H, s).; ESI: 474 (M + H)+ |
| 36 | 1 | 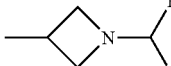 | HCl | NMR: 3.53-3.63 (4H, m), 7.42 (1H, t, J = 7.8 Hz), 8.45 (1H, d, J = 1.0 Hz).; FAB: 366 (M + H)+ |

TABLE 13

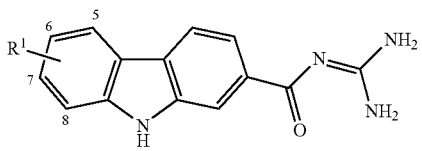

| Ex | Syn | R¹ | Sal | Dat |
|---|---|---|---|---|
| 37 | 2 | 5-F | HCl | NMR: 7.04 (1H, dd, J = 10.3, 7.8 Hz), 7.51 (1H, dt, J = 7.8, 5.6 Hz), 8.35 (1H, s).; FAB: 271 (M + H)+ |
| 38 | 2 | 7-F | HCl | NMR: 7.09 (1H, ddd, J = 9.5, 8.8, 2.5 Hz), 7.35 (1H, dd, J = 9.8, 2.5 Hz), 8.32 (1H, s).; FAB: 271 (M + H)+ |

TABLE 14

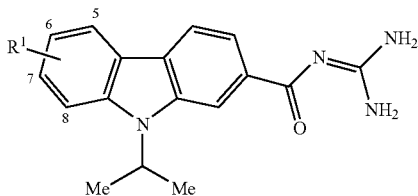

| Ex | Syn | R¹ | Sal | Dat |
|---|---|---|---|---|
| 5 | 5 | 6-NH₂ | 2HCl | NMR: 1.69 (6H, d, J = 6.8 Hz), 7.55 (1H, d, J = 8.8 Hz), 8.74 (1H, s).; FAB: 310 (M + H)+ |
| 39 | 2 | 5-F | HCl | NMR: 1.70 (6H, d, J = 6.8 Hz), 7.08 (1H, dd, J = 10.3, 7.9 Hz), 8.74 (1H, s).; FAB: 313 (M + H)+ |
| 40 | 2 | 6-F | HCl | NMR: 1.68 (6H, d, J = 7.4 Hz), 7.40 (1H, dt, J = 9.3, 2.8 Hz), 8.64 (1H, s).; FAB: 313 (M + H)+ |
| 41 | 2 | 7-F | HCl | NMR: 1.68 (6H, d, J = 6.9 Hz), 7.12 (1H, dt, J = 9.1, 2.0 Hz), 8.64 (1H, s).; FAB: 313 (M + H)+ |

TABLE 14-continued

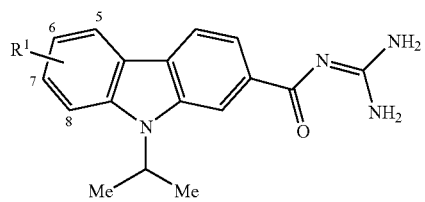

| Ex | Syn | R¹ | Sal | Dat |
|---|---|---|---|---|
| 42 | 2 | 8-F | HCl | NMR: 1.68 (6H, d, J = 6.9 Hz), 7.12 (1H, dt, J = 9.1, 2.0 Hz), 8.64 (1H, s).; FAB: 313 (M + H)+ |
| 43 | 2 | 5-Me | HCl | NMR: 1.69 (6H, d, J = 7.3 Hz), 2.85 (3H, s), 8.64 (1H, s).; FAB: 309 (M + H)+ |
| 44 | 2 | 6-Me | HCl | NMR: 1.67 (6H, d, J = 7.3 Hz), 2.49 (3H, s), 8.62 (1H, s).; FAB: 309 (M + H)+ |
| 45 | 2 | 7-Me | HCl | NMR: 1.69 (6H, d, J = 6.8 Hz), 2.54 (3H, s), 8.55 (1H, s).; FAB: 309 (M + H)+ |
| 46 | 2 | 8-Me | HCl | NMR: 1.75 (6H, d, J = 6.8 Hz), 2.82 (3H, s), 8.47 (1H, s).; FAB: 309 (M + H)+ |
| 47 | 2 | 5-OMe | HCl | NMR: 1.68 (6H, d, J = 6.8 Hz), 4.06 (3H, s), 8.61 (1H, s).; FAB: 325 (M + H)+ |
| 48 | 2 | 6-OMe | HCl | NMR: 1.66 (6H, d, J = 6.9 Hz), 3.87 (3H, s), 8.53 (1H, s).; ESI: 325 (M + H)+ |
| 49 | 2 | 7-OMe | HCl | NMR: 1.69 (6H, d, J = 6.8 Hz), 3.92 (3H, s), 8.56 (1H, s).; FAB: 325 (M + H)+ |
| 50 | 2 | 8-OMe | HCl | NMR: 1.68 (6H, d, J = 6.8 Hz), 4.01 (3H, s), 8.59 (1H, s).; ESI: 325 (M + H)+ |
| 51 | 1 | 5-CN | HCl | NMR: 1.72 (6H, d, J = 6.8 Hz), 7.72 (1H, t, J = 7.3 Hz), 8.79 (1H, s).; FAB: 320 (M + H)+ |
| 52 | 1 | 6-CN | HCl | NMR: 1.71 (6H, d, J = 6.8 Hz), 7.89 (1H, dd, J = 8.8, 1.5 Hz), 8.90 (1H, d, J = 1.5 Hz).; FAB: 320 (M + H)+ |
| 53 | 1 | 7-CN | HCl | NMR: 1.72 (6H, d, J = 7.4 Hz), 7.65 (1H, dd, J = 8.3, 1.0 Hz), 8.71 (1H, s).; FAB: 320 (M + H)+ |
| 54 | 1 | 8-CN | HCl | NMR: 1.83 (6H, d, J = 7.3 Hz), 7.43 (1H, t, J = 7.8 Hz), 8.64 (1H, s).; FAB: 320 (M + H)+ |

TABLE 15

| 55 | 2 | 5-Cl | HCl | NMR: 1.70 (6H, d, J = 6.9 Hz), 7.34 (1H, t, J = 7.8 Hz), 8.72 (1H, s).; FAB: 329 (M + H)+ |
|---|---|---|---|---|
| 56 | 2 | 6-Cl | HCl | NMR: 1.68 (6H, d, J = 6.9 Hz), 7.54 (1H, dd, J = 8.7, 1.9 Hz), 8.65 (1H, s).; FAB: 329 (M + H)+ |

TABLE 15-continued

| | | | | |
|---|---|---|---|---|
| 57 | 2 | 7-Cl | HCl | NMR: 1.69 (6H, d, J = 6.8 Hz), 7.30 (1H, dd, J = 8.3, 2.0 Hz), 8.65 (1H, s).; FAB: 329 (M + H)+ |
| 58 | 2 | 8-Cl | HCl | NMR: 1.76 (6H, d, J = 7.3 Hz), 7.27 (1H, t, J = 7.8 Hz), 8.54 (1H, s).; FAB: 329 (M + H)+ |
| 59 | 1 | 6-NO2 | HCl | NMR: 1.73 (6H, d, J = 6.8 Hz), 8.02 (1H, d, J = 9.2 Hz), 8.77 (1H, s).; FAB: 340 (M + H)+ |
| 60 | 2 | 5-CH2NMe2 | 2HCl | NMR: 1.71 (6H, d, J = 6.8 Hz), 2.89 (6H, s), 8.81 (1H, s).; FAB: 352 (M + H)+ |
| 61 | 2 | 5-CH2OH | HCl | NMR: 1.69 (6H, d, J = 7.3 Hz), 5.10 (2H, s), 8.66 (1H, s).; FAB: 325 (M + H)+ |
| 62 | 2 | 5-CH2OMe | HCl | NMR: 1.70 (6H, d, J = 6.8 Hz), 3.42 (3H, s), 8.65 (1H, s).; FAB: 339 (M + H)+ |
| 63 | 1 | 5-C(O)H | HCl | NMR: 1.73 (6H, d, J = 6.8 Hz), 8.71 (1H, s), 10.44 (1H, s).; FAB: 323 (M + H)+ |

TABLE 16

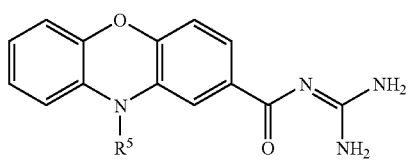

| Ex | Syn | R5 | Sal | Dat |
|---|---|---|---|---|
| 64 | 1 | H | HCl | NMR: 6.49 (1H, dd, J = 7.9, 1.5 Hz), 6.58-6.66 (2H, m), 7.04 (1H, d, J = 2.4 Hz).; FAB: 269 (M + H)+ |
| 65 | 1 | Me | HCl | NMR: 3.14 (3H, s), 6.73-6.80 (3H, m), 7.40 (1H, d, J = 2.0 Hz).; FAB: 283 (M + H)+ |
| 66 | 1 | iPr | HCl | NMR: 1.48 (6H, d, J = 7.0 Hz), 4.37 (1H, sept, J = 7.0 Hz), 7.47 (1H, d, J = 2.0 Hz).; ESI: 311 (M + H)+ |
| 67 | 1 | Et | HCl | NMR: 1.15 (3H, t, J = 6.9 Hz), 3.80 (2H, q, J = 6.9 Hz), 7.40 (1H, d, J = 1.5 Hz).; FAB: 297 (M + H)+ |
| 68 | 1 | cBu | HCl | NMR: 1.68-1.87 (2H, m), 4.38 (1H, tt, J = 7.3, 7.3 Hz), 7.30 (1H, d, J = 1.4 Hz).; FAB: 323 (M + H)+ |
| 69 | 2 | 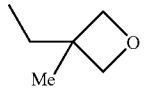 | HCl | NMR: 1.86 (2H, dd, J = 12.2, 2.5 Hz), 2.22 (1H, dd, J = 12.2, 4.4 Hz), 7.61 (1H, s).; FAB: 353 (M + H)+ |
| 70 | 2 | —(CH2)2—NMe2 | 2HCl | NMR: 2.94 (6H, s), 4.19 (2H, t, J = 7.8 Hz), 7.49 (1H, d, J = 1.4 Hz).; EI: 339 (M)+ |

TABLE 16-continued

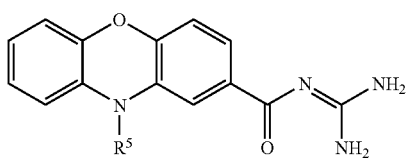

| Ex | Syn | R5 | Sal | Dat |
|---|---|---|---|---|
| 71 | 2 | 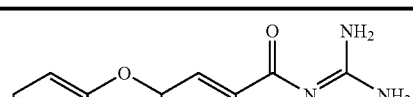 | | NMR: 4.11 (2H, d, J = 5.9 Hz), 4.56 (2H, d, J = 5.9 Hz), 7.28 (1H, d, J = 1.4 Hz).; FAB: 353 (M + H)+ |

TABLE 17

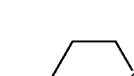

| Ex | Syn | R5 | Sal | Dat |
|---|---|---|---|---|
| 72 | 1 | H | HCl | NMR: 6.51-6.54 (2H, m), 6.64-6.69 (2H, m), 7.29 (1H, d, J = 1.9 Hz).; FAB: 269 (M + H)+ |
| 73 | 1 | Me | HCl | NMR: 3.12 (3H, s), 6.76 (1H, dt, J = 7.3, 1.5 Hz), 7.37 (1H, d, J = 2.0 Hz).; FAB: 283 (M + H)+ |

TABLE 18

| Ex | Syn | Str | Sal | Dat |
|---|---|---|---|---|
| 74 | 1 | 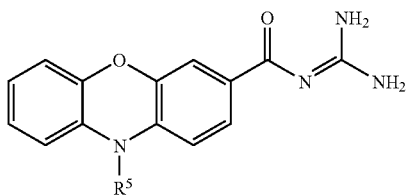 | HCl | NMR: 1.76-1.89 (4H, m), 2.63-2.68 (2H, m), 8.15 (1H, d, J = 1.5 Hz).; FAB: 257 (M + H)+ |

TABLE 18-continued

| Ex | Syn | Str | Sal | Dat |
|---|---|---|---|---|
| 75 | 1 | (structure) | HCl | NMR: 1.71-1.79 (2H, m), 1.79-1.86 (2H, m), 7.11 (1H, t, J = 7.9 Hz).; FAB: 257 (M + H)⁺ |
| 76 | 1 | (structure) | HCl | NMR: 1.20 (3H, t, J = 6.9 Hz), 2.86 (2H, brt, J = 5.3 Hz), 7.18 (1H, t, J = 7.8 Hz).; FAB: 330 (M + H)⁺ |
| 77 | 1 | (structure) | HCl | NMR: 1.22 (3H, t, J = 6.9 Hz), 2.87 (2H, brt, J = 5.6 Hz), 8.18 (1H, s).; FAB: 330 (M + H)⁺ |

TABLE 19

| Ex | Syn | Str | Sal | Dat |
|---|---|---|---|---|
| 78 | 1 | (structure) | HCl | NMR: 7.54 (1H, d, J = 4.4 Hz), 8.05 (1H, s), 8.28 (1H, d, J = 4.4 Hz).; FAB: 272 (M + H)⁺ |
| 7 | 7 | (structure) | HCl | NMR: 5.63 (1H, brs), 7.45 (1H, d, J = 4.9 Hz), 8.12 (1H, s).; FAB: 274 (M + H)⁺ |
| 79 | 1 | (structure) | | NMR: 7.22 (1H, d, J = 4.9 Hz), 7.64 (1H, d, J = 4.9 Hz), 8.10 (1H, s).; ESI: 272 (M + H)⁺ |
| 80 | 7 | (structure) | HCl | NMR: 5.45 (1H, s), 7.28 (1H, d, J = 4.9 Hz), 8.14 (1H, s).; ESI: 274 (M + H)⁺ |

TABLE 19-continued

| Ex | Syn | Str | Sal | Dat |
|---|---|---|---|---|
| 81 | 1 | | HCl | NMR: 3.78-3.85 (2H, m), 7.33 (1H, d, J = 5.2 Hz), 8.44 (1H, d, J = 1.6 Hz).; FAB: 348 (M + H)+ |
| 82 | 1 | | HCl | NMR: 1.63 (3H, s), 7.24 (1H, d, J = 5.2 Hz), 8.16 (1H, d, J = 1.2 Hz).; FAB: 288 (M + H)+ |
| 83 | 1 | | HCl | NMR: 1.66 (3H, s), 2.75 (3H, s), 8.17 (1H, s).; FAB: 302 (M + H)+ |
| 84 | 1 | | HCl | NMR: 4.11-4.16 (1H, m), 7.26 (1H, d, J = 4.9 Hz), 8.27 (1H, d, J = 1.3 Hz).; FAB: 314 (M + H)+ |
| 85 | 1 | | | NMR: 7.92 (1H, d, J = 4.4 Hz), 8.40 (1H, s), 8.80 (1H, s).; FAB: 267 (M + H)+ |
| 86 | 7 | | 2HCl | FAB: 269 (M + H)+ |

TABLE 20

| No | R5 |
|---|---|
| 1 | —C(O)Ph |
| 2 | —S(O)2Ph |

TABLE 21

| No | R5 | R1 |
|---|---|---|
| 3 | Ac | null |
| 4 | —S(O)2Me | null |
| 5 | —C(O)iPr | null |
| 6 | —S(O)2iPr | null |
| 7 | iPr | 6-F |

TABLE 21-continued
| 8 | iPr | 8-F |
| 9 | iPr | 7-Me |
| 10 | iPr | 9-Me |
TABLE 22
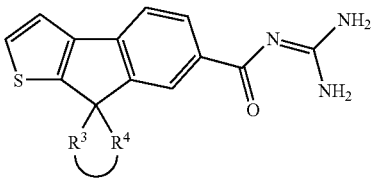
| No |  R³ R⁴ |
|---|---|
| 11 | 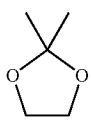 |
| 12 | 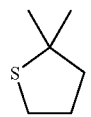 |
| 13 |  |
| 14 |  |
TABLE 23
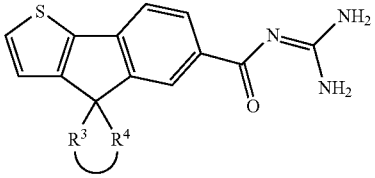
| No |  R³ R⁴ |
|---|---|
| 15 | 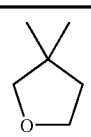 |
TABLE 23-continued
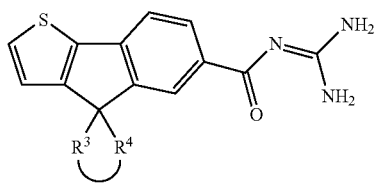
| No |  R³ R⁴ |
|---|---|
| 16 | 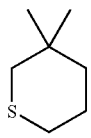 |
| 17 | 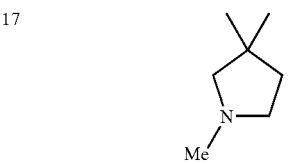 |
| 18 | 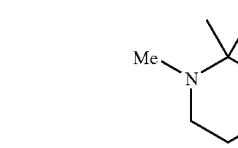 |
TABLE 24
| No | Str |
|---|---|
| 19 | 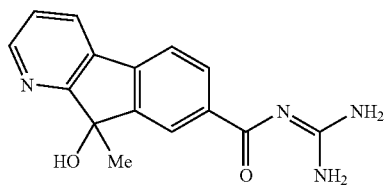 |
| 20 | 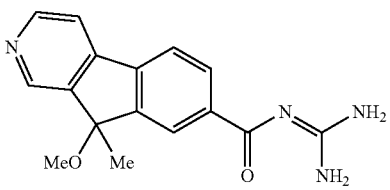 |
| 21 | 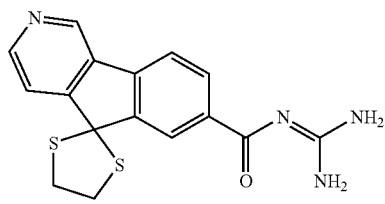 |

TABLE 24-continued

| No | Str |
|---|---|
| 22 | (spiro compound structure: pyrido-fluorene with spiro-tetrahydrofuran and guanidinocarbonyl group) |

INDUSTRIAL APPLICABILITY

Since the compound of the present invention has excellent antagonism to both of 5-$HT_{2B}$ and 5-$HT_7$ receptors, it is useful as a pharmaceutical, particularly as an agent for treating IBS and/or an agent for preventing migraine.

The invention claimed is:

1. An acylguanidine derivative represented by the following general formula (I) or a pharmaceutically acceptable salt thereof (I)

symbols in the formula represent the following meanings
$R^1$ and $R^2$: the same or different from each other, and each represents lower alkyl which may be substituted, lower alkenyl, halogen, —CN, —$NO_2$, —$OR^0$, —O-halogeno-lower alkyl, —OC(O)$R^0$, —$NR^0R^{0a}$, —$NR^0$—C(O)$R^{0a}$, —$NR^0$—S(O)$_2R^{0a}$, —SH, —S(O)$_p$-lower alkyl, —S(O)$_2$—$NR^0R^{0a}$, —C(O)$R^0$, —$CO_2R^0$, —C(O)$NR^0R^{0a}$, cycloalkyl, aryl or a hetero ring group, wherein the aryl and a hetero ring group in $R^1$ and $R^2$ may respectively be substituted,
$R^0$ and $R^{0a}$: the same or different from each other, and each represents —H or lower alkyl,
m, n and p: the same or different from one another and each is 0, 1 or 2,
X: —N($R^5$)—,
Y: a single bond,
$R^5$: —H, lower alkyl which may be substituted, —C(O)$R^0$, —$CO_2R^0$, —C(O)$NR^0R^{0a}$, —S(O)$_p$-lower alkyl, —S(O)$_p$-aryl, cycloalkyl, a hetero ring group, lower alkylene-cycloalkyl, lower alkylene-aryl, lower alkylene-hetero ring group,
—C(O)-aryl or —C(O)-hetero ring group,
wherein the aryl and a hetero ring group in $R^5$ may be respectively substituted, and
ring A: benzene ring.

2. The compound described in claim 1, wherein the substitution position of the guanidinocarbonyl group is the para position against Y.

3. The compound described in claim 2, wherein $R^5$ is lower alkyl, cycloalkyl, lower alkylene-cycloalkyl, a hetero ring group, lower alkylene-(hetero ring group which may be substituted with lower alkyl), —C(O)-lower alkyl or —S(O)$_2$-lower alkyl.

4. The compound described in claim 1 which is selected from the group consisting of
N-(diaminomethylene)-9-isopropyl-9H-carbazole-2-carboxamide, and
N-(diaminomethylene)-5-(hydroxymethyl)-9-isopropyl-9H-carbazole-2-carboxamide, or a pharmaceutically acceptable salt thereof.

5. A pharmaceutical composition which comprises the compound described in claim 1 or a pharmaceutically acceptable salt thereof and a pharmaceutically acceptable carrier.

6. The pharmaceutical composition described in claim 5, which is a 5-$HT_{2B}$ and 5-$HT_7$ receptor antagonist.

7. The pharmaceutical composition described in claim 5, which is a migraine-preventing agent.

8. The pharmaceutical composition described in claim 5, which is an IBS-treating agent.

9. A medicament comprising the acylguanidine derivative of claim 1 or a pharmaceutically acceptable salt thereof, wherein said medicament is a 5-$HT_{2B}$ and 5-$HT_7$ receptor antagonist, a migraine preventing agent and/or an IBS treating agent.

10. A method for preventing migraine and/or treating IBS, which comprises administering an effective amount of the compound described in claim 1 or a salt thereof to a patient.

11. The compound described in claim 3, wherein n is 0.

12. The compound described in claim 11, wherein $R^1$ is chosen from halogen, lower alkyl, —O-lower alkyl, lower alkylene-OH, and —C(O)H.

13. The compound described in claim 12, wherein $R^5$ is lower alkyl.

* * * * *

UNITED STATES PATENT AND TRADEMARK OFFICE
CERTIFICATE OF CORRECTION

PATENT NO. : 8,076,348 B2
APPLICATION NO. : 11/997956
DATED : December 13, 2011
INVENTOR(S) : Hiroyoshi Yamada et al.

It is certified that error appears in the above-identified patent and that said Letters Patent is hereby corrected as shown below:

In claim 1, column 49, in the structure for formula (I) between lines 26-32,

"
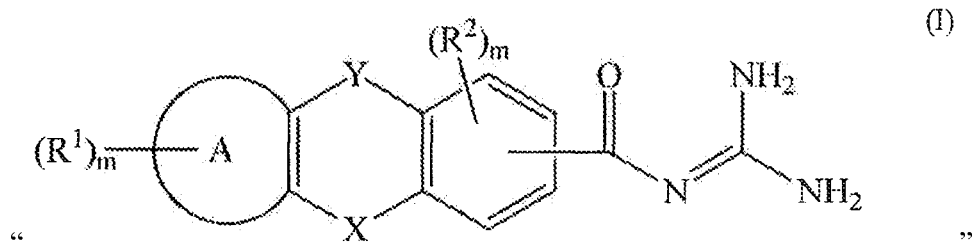
"

should read

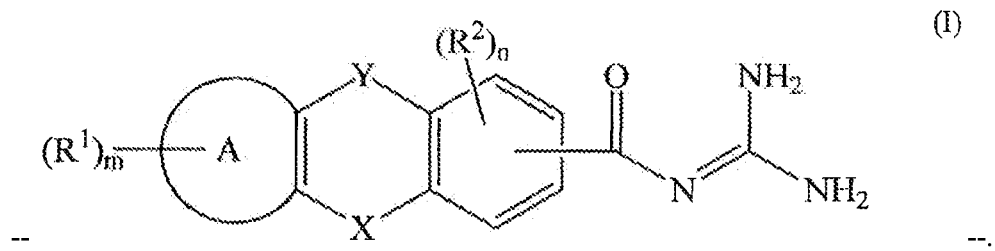
--                                                                                                --.

Signed and Sealed this
Twenty-fifth Day of December, 2012

David J. Kappos
*Director of the United States Patent and Trademark Office*